United States Patent

Willoughby et al.

(10) Patent No.: US 6,531,484 B2
(45) Date of Patent: Mar. 11, 2003

(54) PYRROLIDINE MODULATORS OF CCR5 CHEMOKINE RECEPTOR ACTIVITY

(75) Inventors: Christopher A. Willoughby, Greenbrook, NJ (US); Keith Rosauer, Matawan, NJ (US); Kevin T. Chapman, Scotch Plains, NJ (US); Sander G. Mills, Scotch Plains, NJ (US); Dong-Ming Shen, Edison, NJ (US); Min Shu, Wayne Brook, NJ (US)

(73) Assignee: Merck & co., Inc., Rahway, NJ (US)

( * ) Notice: Subject to any disclaimer, the term of this patent is extended or adjusted under 35 U.S.C. 154(b) by 0 days.

(21) Appl. No.: 09/974,643

(22) Filed: Oct. 10, 2001

(65) Prior Publication Data

US 2002/0198178 A1 Dec. 26, 2002

Related U.S. Application Data

(60) Provisional application No. 60/240,598, filed on Oct. 11, 2000.

(51) Int. Cl.$^7$ .............. A61K 31/46; C07D 451/00; C07D 498/08; C07D 513/08
(52) U.S. Cl. .............. 514/304; 514/224.2; 514/230.5; 514/249; 544/47; 544/105; 544/228; 544/349; 546/23; 546/125; 546/126
(58) Field of Search .................. 546/125, 126, 546/23; 544/47, 105, 238, 349; 514/224.2, 230.5, 249, 304

(56) References Cited

U.S. PATENT DOCUMENTS

| | | | |
|---|---|---|---|
| 5,468,469 A | 11/1995 | Aszalos et al. | |
| 5,684,032 A | 11/1997 | Elliott et al. | |
| 5,776,954 A | 7/1998 | De Laszlo et al. | |
| 6,136,827 A | 10/2000 | Caldwell et al. | |
| 6,140,349 A | 10/2000 | Caldwell et al. | |
| 6,166,037 A | 12/2000 | Budhu et al. | |
| 6,248,755 B1 | 6/2001 | Chapman et al. | |
| 6,265,434 B1 | 7/2001 | Caldwell et al. | |

FOREIGN PATENT DOCUMENTS

| | | |
|---|---|---|
| WO | WO 99/09984 | 3/1999 |
| WO | WO 00/38680 | 7/2000 |
| WO | WO 00/39125 | 7/2000 |

OTHER PUBLICATIONS

T. J. Schall, "Biology of the Rantes/sis Cytokine Family", Cytokine, vol. 3, No. 3, May 1991, pp. 165–183.

P. M. Murphy, "The Molecular Biology of Leukocyte Chenattractant Receptors", Annual Review of Immunology, vol. 12, 1994, pp. 593–633.

H. Deng et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of a C–C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel CC Chemokine Receptor cDNA for a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

A. Chaudhuri et al., "Expression of the Duffy Antigen in K562 Cells,", J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al., "Blocking of HIV–1 Infectivity by a Soluable, Secreted Form of the CD4 Antigen", Science, vol. 238, 1987, pp. 1704–1707.

(List continued on next page.)

*Primary Examiner*—Edward Dentz
(74) *Attorney, Agent, or Firm*—Kenneth R. Walton; Melvin Winokur

(57) ABSTRACT

Pyrrolidine compounds of Formula I:

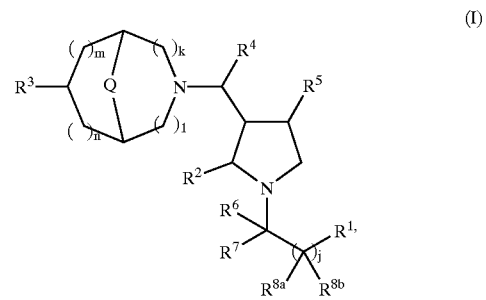

(I)

(wherein $R^1$, $R^2$, $R^3$, $R^4$, $R^5$, $R^6$, $R^7$, $R^{8a}$, $R^{8b}$, j, k, 1, m, and n are defined herein) are described. The compounds are modulators of CCR5 chemokine receptor activity. The compounds are useful, for example, in the prevention or treatment of infection by HIV and the treatment of AIDS, as compounds or pharmaceutically acceptable salts, or as ingredients in pharmaceutical compositions, optionally in combination with other antivirals, immunomodulators, antibiotics or vaccines. Methods of treating AIDS and methods of preventing or treating infection by HIV are also described.

31 Claims, No Drawings

OTHER PUBLICATIONS

J. A. Levy, "Infection by Human Immunodeficiency Virus—DC4 is not Enough", N. Eng. J. Med., vol. 335, No. 20, Nov. 1996), pp. 1528–1530.

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistence to HIV–1 infection in caucasian individuals bearing mutant alleles of the CCR–5 cehmokine receptor gene", Nature, vol. 382, Aug. 1996, pp. 722–725.

C. M. Hill et al., "Natural resistance to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

H. Hotoda, "Small–molecule inhibitors of HIV–1 entry via chemokine receptors", Drugs of the Future, vol. 24, No. 12, 1999, pp. 1355–1362.

R. Horuk et al., "Chemokine Receptor Antagonists", Med. Res. Rev., vol. 20, No. 2, 2000, pp. 155–168.

M. Shiraishi et al., "Discovery of Novel, Potent , and Selective Small–Molecule CCR5 Antagonists as Anti–HIV–1 Agents: Synthesis and Biological Evaluation of Anilide Derivatives with a Quanternary Ammonium Moiety", J. Med. Chem., vol. 43, 2000, pp. 2049–2063.

PYRROLIDINE MODULATORS OF CCR5 CHEMOKINE RECEPTOR ACTIVITY

This application claims the benefit of U.S. Provisional Application No. 60/240,598, filed Oct. 11, 2000, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR2A and CCR2B (or "CKR-2A"/"CKR-2A" or "CC-CKR-2A"/"CC-CKR-2A") [MCP-1, MCP-3, MCP-4]; CCR3 (or "CKR-3" or "CC-CKR-3") [eotaxin, RANTES, MCP-3] (Combadiere, et al., *J. Biol. Chem.*, 270, 16491–16494 (1995); CCR4 (or "CKR-4" or "CC-CKR-4") [MIP-1$\alpha$, RANTES, MCP-1] (Power, et al., *J. Biol. Chem.*, 270, 19495–19500 (1995)); CCR5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR1, CCR2, CCR2A, CCR2B, CCR3, CCR4, CCR5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR5 and inhibits the binding of the natural CCR5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR5 receptors which are not expressed on the cell surface appear to be unusually resistant to HIV-1 infection and are not immunocompromised by the presence of this genetic variant (*Nature*, 382, 722–725 (1996)). Absence of CCR5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR5 or fusin, some can use both as well as the related CCR2B and CCR3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+T cells have been characterized as the β-chemokines RANTES, MIP-1α and MIP-1β.

The following references are of interest as background:

WO 00/38680 discloses certain azabicycloalkanes to be useful as CCR5 modulators.

WO 00/39125 discloses certain piperidines to be useful as CCR5 modulators.

SUMMARY OF THE INVENTION

The present invention is directed to compounds which inhibit the entry of human immunodeficiency virus (HIV) into target cells and are of value in the prevention of infection by HIV, the treatment of infection by HIV, the prevention and/or treatment of the resulting acquired immune deficiency syndrome (AIDS), and the delay in the onset of AIDS. The present invention also relates to pharmaceutical compositions containing the compounds and to a method of use of the present compounds and other agents for the prevention and treatment of AIDS and viral infection by HIV.

The present invention is further directed to compounds which are modulators of CCR5 chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention includes compounds of Formula I:

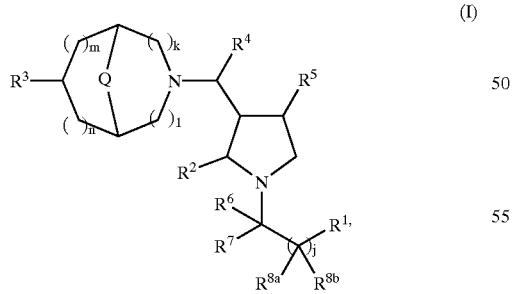

(I)

wherein:
  $R^1$ is selected from:
  (1) —$CO_2H$,
  (2) —$NO_2$,
  (3) -tetrazolyl,
  (4) -hydroxyisoxazole,
  (5) —$SO_2NHCO$—($C_{0-3}$ alkyl)-$R^9$, wherein $R^9$ is independently selected from hydrogen, $C_{1-6}$ alkyl, $C_{5-6}$ cycloalkyl, benzyl or phenyl, wherein alkyl, cycloalkyl, benzyl or phenyl is unsubstituted or substituted with 1–3 substituents independently selected from halo, $C_{1-3}$ alkyl, —O—$C_{1-3}$ alkyl and trifluoromethyl, and
  (6) —$P(O)(OH)_2$;
j is an integer which is 0, 1, 2 or 3;
$R^2$ is hydrogen or $C_{1-6}$ alkyl;
Q is —$(CH_2)_{1-3}$—, —$CH_2OCH_2$—, —$CH_2SCH_2$—, —$CH_2S(O)CH_2$—, —$CH_2S(O_2)CH_2$—, or —$CH_2N(R^d)CH_2$—;
k, l, m and n are each independently integers from zero to 3;
$R^3$ is phenyl, naphthyl, or heterocycle, wherein any one of which is optionally substituted with from 1 to 7 of $R^{11}$ where $R^{11}$ is independently selected from:
  (a) halo,
  (b) cyano,
  (c) hydroxy,
  (d) $C_{1-6}$ alkyl, which is unsubstituted or substituted with 1–5 of $R^{12}$ where $R^{12}$ is independently selected from halo, cyano, hydroxy, —O—$C_{1-6}$ alkyl, —$C_{3-6}$ cycloalkyl, —$CO_2H$, —$CO_2$—($C_{1-6}$ alkyl), —$CF_3$, —$SO_2R^9$, —$NR^9R^{10}$ (where $R^9$ is independently as defined above and $R^{10}$ is independently selected from the definitions of $R^9$), phenyl, naphthyl, biphenyl, and heterocycle;
    wherein phenyl, naphthyl, biphenyl, or heterocycle is unsubstituted or substituted with 1–7 of $R^{13}$ where $R^{13}$ is independently selected from halo, cyano, hydroxy, $C_{1-6}$ alkyl, $C_{1-6}$ haloalkyl, —O—$C_{1-6}$ alkyl, —O—$C_{1-6}$ haloalkyl, —$CO_2H$, —$CO_2$($C_{1-6}$ alkyl), —$NR^9R^{10}$, —($C_{1-6}$ alkyl)—$NR^9R^{10}$, —$SO_2R^9$, —($C_{1-6}$ alkyl)hydroxy, —O—$C_{3-6}$ cycloalkyl, benzyloxy, phenoxy, and —$NO_2$,
  (e) —O—$C_{1-6}$ alkyl, which is unsubstituted or substituted with 1–5 of $R^{12}$,
  (f) —O-phenyl, which is unsubstituted or substituted with 1–5 of $R^{13}$,
  (g) —O-heterocycle, which is unsubstituted or substituted with 1–5 of $R^{13}$,
  (h) —$NO_2$,
  (i) phenyl,
  (j) —$CO_2R^9$,
  (k) tetrazolyl,
  (l) —$NR^9R^{10}$,
  (m) —$NR^9$—$COR^{10}$,
  (n) —$NR^9$—$CO_2R^{10}$,
  (o) —CO—$NR^9R^{10}$,
  (p) —OCO—$NR^9R^{10}$,
  (q) —$NR^9CO$—$NR^9R^{10}$,
  (r) —$S(O)_m$—$R^9$, wherein m is an integer selected from 0, 1 and 2,
  (s) —$S(O)_2$—$NR^9R^{10}$,
  (t) —$NR^9S(O)_2$—$R^{10}$,
  (u) —$NR^9S(O)_2$—$NR^9R^{10}$,
  (v) $C_{2-6}$ alkenyl,
  (w) furanyl, which is unsubstituted or substituted with benzyl which is unsubstituted or substituted with 1–7 of $R^{13}$ wherein $R^{13}$ is independently as defined above,
  (x) —$C_{3-6}$ cycloalkyl,
  (y) —O—$C_{3-6}$ cycloalkyl, and
  (y) oxo;
$R^4$ is hydrogen or $C_{1-6}$ alkyl;
$R^5$ is phenyl, naphthyl, or heterocycle, wherein any one of which is unsubstituted or substituted with 1–7 substituents where the substituents are independently selected from:

(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^6$ is hydrogen, $C^{1-10}$ alkyl, $C_{3-8}$ cycloalkyl, —($C_{1-3}$ alkyl)-$C_{3-8}$ cycloalkyl, —($C_{0-2}$ alkyl)-($C_{3-8}$ cycloalkylidenyl)-($C_{1-2}$ alkyl), $C_{2-10}$ alkenyl, $C_{2-10}$ alkynyl, cyclohexenyl, phenyl, —($C_{1-6}$ alkyl)-phenyl, naphthyl, dihydronaphthyl, tetrahydronaphthyl, octahydronaphthyl, biphenyl, or heterocycle; wherein any of which except for hydrogen is unsubstituted or substituted with 1–7 of $R^{11}$ where $R^{11}$ is independently as defined above;

$R^7$ is hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

or alternatively $R^6$ and $R^7$ together with the carbon atom to which they are attached form a $C_{3-8}$ cycloalkyl ring which may be unsubstituted or substituted with 1–7 of $R^{11}$;

$R^{8a}$ and $R^{8b}$ are each independently hydrogen, $C_{1-6}$ alkyl, $C_{2-6}$ alkenyl, $C_{2-6}$ alkynyl, $C_{3-8}$ cycloalkyl, phenyl, naphthyl, or heterocycle; wherein any one of which except hydrogen is unsubstituted or substituted with 1–7 substituents where the substituents are independently selected from:
(a) halo,
(b) $C_{1-4}$ haloalkyl,
(c) hydroxy,
(d) $C_{1-4}$ alkyl,
(e) —O—$C_{1-4}$ alkyl,
(f) —O—$C_{1-4}$ haloalkyl,
(g) $C_{3-8}$ cycloalkyl,
(h) —$CO_2R^a$,
(i) —$NR^aR^b$, and
(j) —$CONR^aR^b$;

or alternatively $R^{8a}$ and $R^{8b}$ together with the carbon atom to which they are attached form:
(a) a 3- to 8-membered saturated carbocyclic ring,
(b) a 4- to 8-membered monocyclic heterocycle containing from 1 to 3 heteroatoms selected from nitrogen, oxygen and sulfur,
(c) a 5- to 8-membered saturated carbocyclic ring to which is fused a $C_{3-8}$ cycloalkyl, or
(d) a 5- to 8-membered heterocyclic ring containing from 1 to 3 heteroatoms selected from nitrogen, oxygen and sulfur, to which is fused a $C_{3-8}$ cycloalkyl,
wherein the ring system of (a), (b), (c) or (d) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, and hydroxy;
or a pharmaceutically acceptable salt thereof.

A first embodiment of the present invention is a compound of Formula I, wherein $R^1$ is selected from —$CO_2H$ and -tetrazolyl;
and all other variables are as originally defined;
or a pharmaceutically acceptable salt thereof.
In one aspect of the first embodiment, $R^1$ is —$CO_2H$.
A second embodiment of the present invention is a compound of Formula I, wherein $R^2$ is hydrogen;
and all other variables are as originally defined;
or a pharmaceutically acceptable salt thereof.
A third embodiment of the present invention is a compound of Formula I, wherein $R^3$ is
(i) phenyl,
(ii) a 5-membered monocyclic heterocycle containing two nitrogen atoms, which is optionally substituted on one of its ring carbons with oxo and which is optionally fused with a benzene ring, or
(iii) a 5-membered monocyclic heterocycle containing two nitrogen atoms, which is optionally fused with a 5- or 6-membered heterocycle containing 1 or 2 nitrogen atoms and which is optionally substituted on any one of its ring carbons with oxo;
wherein any one of phenyl (i), heterocycle (ii), or heterocycle (iii) is optionally substituted with 1–7 substituents independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from halo, cyano, hydroxy, —O—$C_{1-6}$ alkyl, —$C_{3-5}$ cycloalkyl, —$CO_2H$, —$CO_2(C_{1-6}$ alkyl), —$CF_3$, —$SO_2R^9$, —$NR^9R^{10}$,
where $R^9$ and $R^{10}$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl, phenyl, naphthyl, biphenyl, and heterocycle, which is unsubstituted or substituted with 1–7 of $R^{13}$ where $R^{13}$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^9$ and —$NR^9R^{10}$,
(e) —O—$C_{1-6}$ alkyl, which is unsubstituted or substituted with 1–5 of $R^{12}$,
(f) —$NO_2$,
(g) phenyl,
(h) —$CO_2R^9$,
(i) tetrazolyl,
(j) —$NR^9R^{10}$,
(k) —$NR^9$—$COR^{10}$,
(l) —$NR^9$—$CO_2R^{10}$,
(m) —CO—$NR^9R^{10}$,
(n) —OCO—$NR^9R^{10}$,
(o) —$NR^9CO$—$NR^9R^{10}$,
(p) —$S(O)_p$—$R^9$, wherein p is an integer selected from 0, 1 and 2,
(q) —$S(O)_2$—$NR^9R^{10}$,
(r) —$NR^9S(O)_2$—$R^{10}$,
(s) —$NR^9S(O)_2$—$NR^9R^{10}$;
(t) —$C_{3-6}$ cycloalkyl, and
(u) —O—$C_{3-6}$ cycloalkyl;
and all other variables are as originally defined;
or a pharmaceutically acceptable salt thereof.

In one aspect of the third embodiment, $R^3$ is a heterocycle selected from the group consisting of:

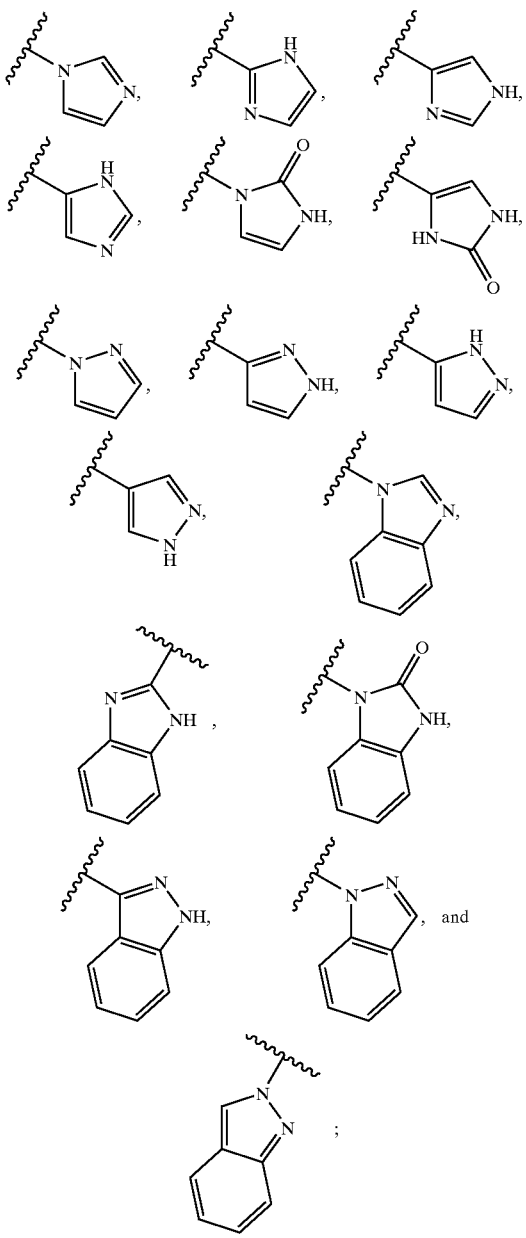

wherein "⌇⌇⌇" denotes the point of attachment and wherein the heterocycle is optionally substituted with from 1 to 5 substituents independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from halo, cyano, hydroxy, —O—$C_{1-6}$ alkyl, —$C_{3-5}$ cycloalkyl, —$CO_2H$, —$CO_2$($C_{1-6}$ alkyl), —$CF_3$, —$SO_2R^9$, —$NR^9R^{10}$,
where $R^9$ and $R^{10}$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl, phenyl, naphthyl, biphenyl, and heterocycle, which is unsubstituted or substituted with 14 7 of $R^{13}$ where $R^{13}$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2$($C_{1-6}$ alkyl), —$CF_3$, —$OCF_3$, —$SO_2R^9$ and —$NR^9R^{10}$,
(e) —O—$C_{1-6}$ alkyl, which is unsubstituted or substituted with 1–5 of $R^{12}$,
(f) —$NO_2$,
(g) phenyl,
(h) —$CO_2R^9$,
(i) tetrazolyl,
(j) —$NR^9R^{10}$,
(k) —$NR^9$—$COR^{10}$,
(l) —$NR^9$—$CO_2R^{10}$,
(m) —CO—$NR^9R^{10}$,
(n) —OCO—$NR^9R^{10}$,
(o) —$NR^9CO$—$NR^9R^{10}$,
(p) —S(O)$_p$—$R^9$, wherein p is an integer selected from 0, 1 and 2,
(q) —S(O)$_2$—$NR^9R^{10}$,
(r) —$NR^9S(O)_2$—$R^{10}$,
(s) —$NR^9S(O)_2$—$NR^9R^{10}$;
(t) —$C_{3-6}$ cycloalkyl, and
(u) —O—$C_{3-6}$ cycloalkyl.

In another aspect of the third embodiment, $R^3$ is

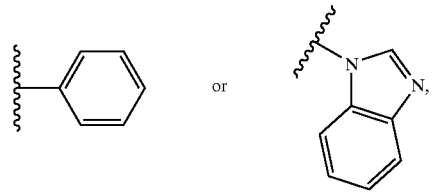

which is optionally substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—$(C_{1-2}$ alkyl)
(j) phenyl,
(k) $C_{1-6}$ alkyl, which is unsubstituted or substituted with phenyl, which is unsubstituted or substituted with 1–4 of $R^f$ where $R^f$ is independently selected from halo, cyano, hydroxy, —O—$C_{1-6}$ alkyl, —O—$C_{3-5}$ cycloalkyl, —$CO_2H$, —$C_{02}$($C_{1-6}$ alkyl), —$CF_3$, —$OCF_3$, and —$SO_2$—($C_{1-3}$alkyl),
(l) —O—$C_{1-6}$ alkyl,
(m) —$C_{3-5}$ cycloalkyl,
(n) —$CH_2$—($C_{3-5}$ cycloalkyl), and
(o) —O—$C_{1-6}$ alkyl.

A fourth embodiment of the present invention is a compound of Formula I, wherein $R^4$ is hydrogen; and all other variables are as originally defined; or a pharmaceutically acceptable salt thereof.

A fifth embodiment of the present invention is a compound of Formula I, wherein $R^4$ is methyl;
and all other variables are as originally defined;
or a pharmaceutically acceptable salt thereof.

A sixth embodiment of the present invention is a compound of Formula I, wherein $R^5$ is phenyl, thienyl, pyrazolyl, thiazolyl, thiadiazolyl, furanyl, oxadiazolyl, pyrazinyl, pyrimidinyl, or pyridyl, any one of which is unsubstituted or substituted with 1–5 substituents where the substituents are independently selected from:
  (a) halo,
  (b) trifluoromethyl,
  (c) hydroxy,
  (d) $C_{1-3}$ alkyl, and
  (e) —O—$C_{1-3}$ alkyl;
and all other variables are as originally defined;
or a pharmaceutically acceptable salt thereof.

In one aspect of the sixth embodiment, $R^5$ is phenyl or thienyl, either of which is unsubstituted or substituted with 1–5 substituents where the substituents are independently selected from:
  (a) halo,
  (b) —$CF_3$,
  (c) hydroxy, and
  (d) $C_{1-3}$ alkyl.

In another aspect of the sixth embodiment, $R^5$ is phenyl, which is optionally substituted with from 1 to 5 substituents independently selected from fluoro and chloro, or unsubstituted thienyl.

In still another aspect of the sixth embodiment, $R^5$ is phenyl, 3-fluorophenyl, or 3-thienyl.

A seventh embodiment of the present invention is a compound of Formula I, wherein
  Q is —$CH_2$—, —$(CH_2)_2$—, —$CH_2OCH_2$—, or —$CH_2SCH_2$—;
  k and l are each independently integers from zero to 1; and
  m and n are each independently integers equal to 1 or 2;
  and all other variables are as originally defined;
or a pharmaceutically acceptable salt thereof.

In one aspect of the seventh embodiment, Q is —$(CH_2)_2$—, —$CH_2OCH_2$—, or —$CH_2SCH_2$—;
  k and l are each integers equal to zero; and
  m and n are each integers equal to 1.

An eighth embodiment of the present invention is a compound of Formula I, wherein $R^6$ is $C_{1-10}$ alkyl, $C_{3-8}$ cycloalkyl, or —($C_{1-3}$ alkyl)-$C_{3-8}$ cycloalkyl, any one of which is unsubstituted or substituted with 1–5 substituents where the substituents are independently selected from:
  (a) halo,
  (b) hydroxy,
  (c) —$C_{1-6}$ alkyl, which is unsubstituted or substituted with cyano, —$CO_2H$, hydroxy or trifluoromethyl,
  (d) —O—$C_{1-6}$ alkyl, which is unsubstituted or substituted halo, cyano, —$CO_2H$, hydroxy or trifluoromethyl,
  (e) —$CF_3$,
  (f) —$CHF_2$,
  (g) —$CH_2F$, and
  (h) —$CO_2H$;
and all other variables are as originally defined;
or a pharmaceutically acceptable salt thereof.

A ninth embodiment of the present invention is a compound of Formula I, wherein $R^7$ is hydrogen;
and all other variables are as originally defined;
or a pharmaceutically acceptable salt thereof.

In an aspect of the ninth embodiment, j is an integer equal to zero.

A tenth embodiment of the present invention is a compound of Formula I, wherein $R^6$ and $R^7$ are both hydrogen;
and all other variables are as originally defined;
or a pharmaceutically acceptable salt thereof.

An eleventh embodiment of the present invention is a compound of Formula I, wherein $R^{8a}$ and $R^{8b}$ are each independently hydrogen, $C_{1-6}$ alkyl or $C_{3-6}$ cycloalkyl, wherein the alkyl or cycloalkyl is unsubstituted or substituted with 1–7 substituents independently selected from:
  (a) halo,
  (b) —$CF_3$,
  (c) hydroxy, and
  (d) —O—$C_{1-3}$ akyl;
or $R^{8a}$ and $R^{8b}$ together with the carbon atom to which they are attached form:
  (a) a 3- to 6-membered saturated carbocyclic ring,
  (b) a 4- to 6-membered saturated heterocyclic ring containing one oxygen atom, or
  (c) a 5- or 6-membered saturated carbocyclic ring to which is fused a $C_{3-6}$ cycloalkyl;
  wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy;
and all other variables are as originally defined;
or a pharmaceutically acceptable salt thereof.

A twelfth embodiment of the present invention is a compound of Formula I, wherein j is an integer equal to 1;
and all other variables are as originally defined;
or a pharmaceutically acceptable salt thereof.

A thirteenth embodiment of the present invention is a compound of Formula I, wherein:
  $R^6$ and $R^7$ are both hydrogen;
  $R^{8a}$ and $R^{8b}$ are each independently hydrogen, $C_{1-6}$ alkyl or $C_{3-6}$ cycloalkyl, wherein the alkyl or cycloalkyl is unsubstituted or substituted with 1–7 substituents independently selected from:
    (a) halo,
    (b) —$CF_3$,
    (c) hydroxy, and
    (d) —O—$C_{1-3}$ alkyl;
  or $R^{8a}$ and $R^{8b}$ together with the carbon atom to which they are attached form:
    (a) a 3- to 6-membered saturated carbocyclic ring,
    (b) a 4- to 6-membered saturated heterocyclic ring containing one oxygen atom, or
    (c) a 5- or 6-membered saturated carbocyclic ring to which is fused a $C_{3-6}$ cycloalkyl;
    wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy; and
  j is an integer equal to 1;
and all other variables are as originally defined;
or a pharmaceutically acceptable salt thereof.

It is to be understood that additional embodiments of the present invention include, but are not limited to, compounds of Formula I wherein each of two or three or more of Q, $R^1$, $R^2$, $R^3$, $R^4$, $R^5$, $R^6$, $R^7$, $R^{8a}$, $R^{8b}$, j, k, l, m, and n is independently defined in accordance with one of the foregoing embodiments or aspects thereof as set forth above. Any and all possible combinations of these variables in Formula I are within the scope of the present invention.

The compounds of the instant invention have at least two asymmetric centers at the ring junction of the substituents bearing $R^4$ and $R^5$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

A first class of compounds of the present invention are compounds having the trans orientation, depicted as:

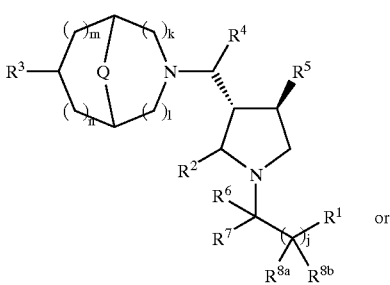

or

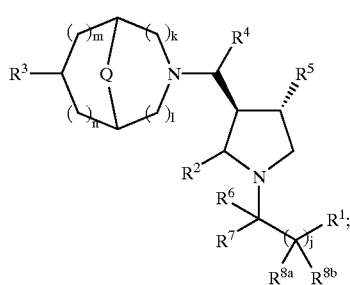

and pharmaceutically acceptable salts thereof.

A second class of the present invention is compounds of Formula (II):

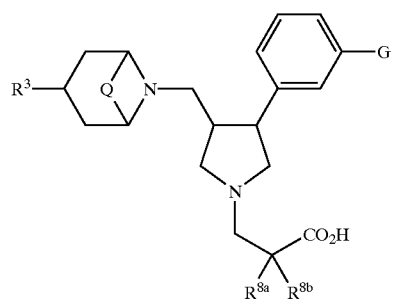

(II)

wherein
G is hydrogen or fluoro;
Q is —(CH$_2$)$_2$—, —CH$_2$OCH$_2$—, or —CH$_2$SCH$_2$—;

$R^3$ is:

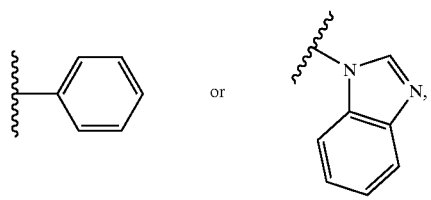

which is optionally substituted with 1–5 substituents where the substituents are independently selected from:
(a) halo,
(b) cyano,
(c) —NO$_2$,
(d) —CF$_3$,
(e) —CHF$_2$,
(f) —CH$_2$F,
(g) phenyl,
(h) C$_{1-6}$ alkyl, which is unsubstituted or substituted with phenyl, which is unsubstituted or substituted with 1–4 of $R^{13}$ where $R^{13}$ is independently selected from halo, cyano, hydroxy, —O—C$_{1-6}$ alkyl, —CO$_2$H, —CO$_2$(C$_{1-6}$ alkyl), and trifluoromethyl, and
(i) —O—C$_{1-6}$ alkyl;

$R^{8a}$ and $R^{8b}$ are each hydrogen, C$_{1-3}$ alkyl, or C$_{3-6}$ cycloalkyl;

or each of $R^{8a}$ and $R^{8b}$ is independently C$_{1-3}$ alkyl;

or $R^{8a}$ and $R^{8b}$ together with the carbon atom to which they are attached form:

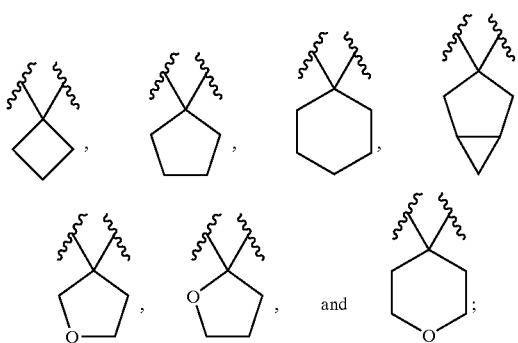

or a pharmaceutically acceptable salt thereof.

In a sub-class of the second class are compounds of Formula (III):

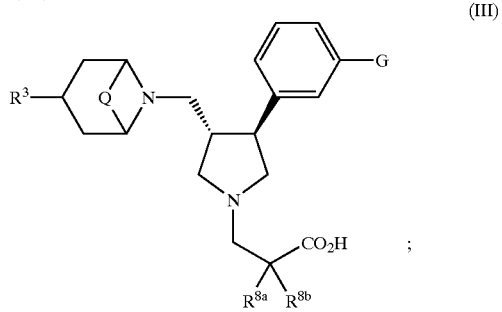

(III)

wherein the variables are as defined above for the second class;
or a pharmaceutically acceptable salt thereof.

A third class of the present invention is a compound of Formula (IV):

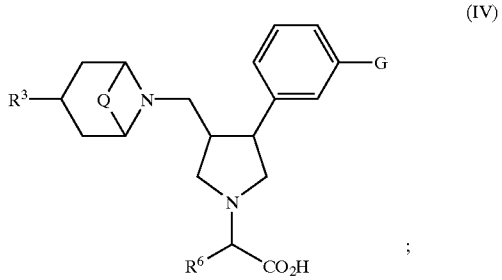

(IV)

wherein
G is hydrogen or fluoro;
Q is —(CH$_2$)$_2$—, —CH$_2$OCH$_2$—, or —CH$_2$SCH$_2$—;
R$^3$ is:

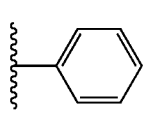 or 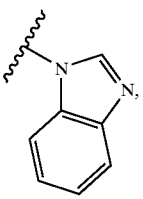

which is optionally substituted with 1–5 substituents where the substituents are independently selected from:
(a) halo,
(b) cyano,
(c) —NO$_2$,
(d) —CF$_3$,
(e) —CHF$_2$,
(f) —CH$_2$F,
(g) phenyl,
(h) C$_{1-6}$ alkyl, which is unsubstituted or substituted with phenyl, which is unsubstituted or substituted with 1–4 of R$^{13}$ where R$^{13}$ is independently selected from halo, cyano, hydroxy, —O—C$_{1-6}$ alkyl, —CO$_2$H, —CO$_2$(C$_{1-6}$ alkyl), and trifluoromethyl, and
(i) —O—C$_{1-6}$ alkyl;

R$^6$ is isopropyl, isobutyl, sec-butyl, t-butyl, cyclohexyl, cyclopentyl, cyclobutyl, cyclopropyl, —CH$_2$-cyclohexyl, —CH$_2$-cyclopentyl, —CH$_2$-cyclobutyl, and —CH$_2$-cyclopropyl;
or a pharmaceutically acceptable salt thereof.

In a sub-class of the third class are compounds of Formula V:

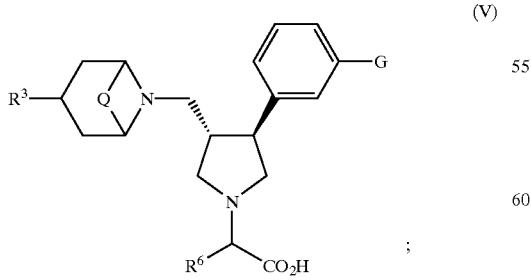

(V)

wherein the variables are as defined above for the third class;
or a pharmaceutically acceptable salt thereof.

The independent syntheses of the diastereomers described above or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Other embodiments of the present invention include the following:
Other embodiments of the present invention include the following:

(a) A pharmaceutical composition comprising a compound of Formula (I) and a pharmaceutically acceptable carrier.
(b) The pharmaceutical composition of (a), further comprising at least one antiviral selected from the group consisting of HIV protease inhibitors, non-nucleoside HIV reverse transcriptase inhibitors, and nucleoside HIV reverse transcriptase inhibitors.
(c) A method for modulating (e.g., inhibiting) CCR5 chemokine receptor activity in a subject which comprises administering to the subject an effective amount of the compound of Formula (I).
(d) A method of preventing or treating infection by HIV in a subject in need thereof which comprises administering to the subject a therapeutically effective amount of a compound of Formula (I).
(e) The method of (d), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.
(f) A method of delaying the onset or AIDS or treating AIDS in a subject in need thereof which comprises administering to the subject a therapeutically effective amount of a compound of Formula (I).
(g) The method of (f), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors
(h) A method of modulating (e.g., inhibiting) CCR5 chemokine receptor acitivity in a subject in need thereof which comprises administering to the subject a therapeutically effective amount of the composition of (a) or (b).
(i) A method of preventing or treating infection by HIV in a subject in need thereof which comprises administering to the subject a therapeutically effective amount of the composition of (a) or (b).
(j) A method of treating AIDS or delaying the onset of AIDS in a subject in need thereof which comprises administering to the subject a therapeutically effective amount of the composition of (a) or (b).

Still other embodiments of the present invention include the following:
(k) A pharmaceutical composition which comprises the product prepared by combining (e.g., mixing) an effective amount of a compound of Formula (I) and a pharmaceutically acceptable carrier.
(l) A combination useful for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(m) The combination of (l), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

Additional embodiments of the invention include the pharmaceutical compositions and methods set forth in (a)–(j) above and the compositions and combinations set forth in (k)–(m), wherein the compound employed therein is a compound of one of the embodiments, classes, sub-classes, or aspects of compounds described above. In all of these embodiments, the compound may optionally be used in the form of a pharmaceutically acceptable salt.

As used herein, the term "$C_{1-6}$ alkyl" (or "$C_1$-$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. Similar terms such as "$C_{1-10}$ alkyl" have analogous meanings.

The term "$C_0$" as employed in expressions such as "$C_{0-6}$ alkyl" means a direct covalent bond.

The term "$C_{2-6}$ alkenyl" (or "$C_2$-$C_6$ alkenyl") means linear or branched chain alkenyl groups having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-10}$ alkenyl" have analogous meanings.

The term "$C_{2-6}$ alkynyl" (or "$C_2$–$C_6$ alkynyl") means linear or branched chain alkynyl groups having from 2 to 6 carbon atoms and includes all of the hexynyl and pentynyl isomers as well as 1-butynyl, 2-butynyl, 3-butynyl, 1-propynyl, 2-propynyl, and ethynyl (or acetylenyl). Similar terms such as "$C_{2-10}$ alkynyl" have analogous meanings.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The term "$C_{3-6}$ cycloalkyl" refers to a cyclic ring selected from cyclopropyl, cyclobutyl, cyclopentyl, and cyclohexyl. Similar terms such as "$C_{5-6}$ cycloalkyl" have analogous meanings.

The term "halogen" (or "halo") refers to fluorine, chlorine, bromine and iodine (alternatively, fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. Similarly, "$C_{1-6}$ fluoroalkyl" means a $C_1$ to $C_6$ linear or branched alkyl group as defined above with one or more fluorine substituents. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "—($C_{1-6}$ alkyl)hydroxy" refers to a $C_{1-6}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "$C_{3-8}$ cycloalkylidenyl" refers to a $C_{3-8}$ cycloalkyl group as defined above in which one of the ring carbons is attached to each of two carbon atoms not in the ring such that the three carbon atoms form a carbon chain or part of a carbon chain. Thus, "—($C_{0-2}$ alkyl)-($C_{3-8}$ cycloalkylidenyl)-($C_{1-2}$ alkyl)" refers to and encompasses such groups as:

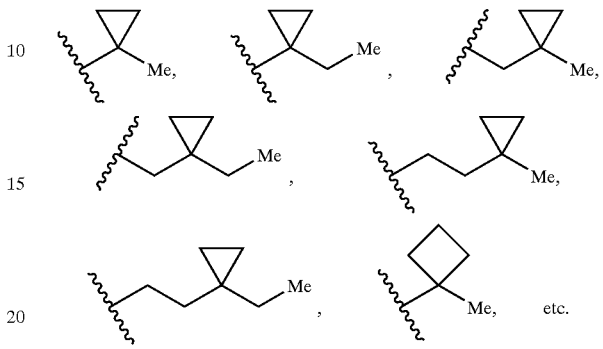

The term "carbocycle" (and variations thereof such as "carbocyclic" or "carbocyclyl") as used herein broadly refers to a $C_3$ to $C_8$ monocyclic, saturated or unsaturated ring or a $C_7$ to $C_{14}$ bicyclic ring system in which the rings are independent or fused and in which each ring is saturated or unsaturated.

The term "aryl" refers to aromatic mono- and poly-carbocyclic ring systems, wherein the individual carbocyclic rings in the polyring systems may be fused or attached to each other via a single bond. Suitable aryl groups include, but are not limited to, phenyl, naphthyl, and biphenylenyl.

The term "heterocycle" (and variations thereof such as "heterocyclic" or "heterocyclyl") broadly refers to a 4- to 8-membered monocyclic ring, 7- to 14-membered bicyclic ring system, or an 11 to 16-membered tricyclic ring system, any ring of which is saturated or unsaturated, and which consists of carbon atoms and one or more heteroatoms (e.g., from 1 to 4 heteroatoms) selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothipheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms have the same meaning: "indazolyl" and "benzopyrazolyl"; "pyridinyl" and "pyridyl".

Unless expressly set forth to the contrary, an "unsaturated" ring is a partially or fully unsaturated ring.

The term "substituted" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups.

It is understood that the definition of a substituent at a particular location in a molecule is independent of its definition at other locations in the molecule. Thus, for example, when $R^3$=alkyl substituted with 1–5 of $R^{12}$ (defined elsewhere), each $R^{12}$ is independently selected from the possible values thereof; i.e., each $R^{12}$ can be the same as or different from any other $R^{12}$.

Exemplifying the invention is the use of the compounds disclosed in the Examples.

Exemplary compounds of the present invention include compounds selected from the group consisting of:

(2R)-[(3R,4S)-3-{[3-exo-(1H-Benzimidazol-1-yl)-8-azabicyclo[3.2.1]oct-8-yl]methyl}-4-(3-fluorophenyl) pyrrolidin-1-yl](cyclohexyl)ethanoic acid;

(2R)-Cyclohexyl((3S,4R)-3-(3-fluorophenyl)-4-{[3-exo-(2-methyl-1H-benzimidazol-1-yl)-8-azabicyclo[3.2.1]oct-8-yl]methyl}pyrrolidin-1-yl)ethanoic acid;

(2R)-Cyclohexyl[(3R,4S)-3-{[3-exo-(2-ethyl-1H-benzimidazol-1-yl)-8-azabicyclo[3.2.1]oct-8-yl]methyl}-4-(3-fluorophenyl)pyrrolidin-1-yl]ethanoic acid;

(2R)-[(3R,4S)-3-{[3-endo-(1H-Benzimidazol-1-yl)-8-azabicyclo[3.2.1]oct-8-yl]methyl}-4-(3-fluorophenyl) pyrrolidin-1-yl](cyclohexyl)ethanoic acid;

(2R)-Cyclohexyl((3S,4R)-3-(3-fluorophenyl)-4-{[3-endo-(2-methyl-1H-benzimidazol-1-yl)-8-azabicyclo[3.2.1] oct-8-yl]methyl}pyrrolidin-1-yl)ethanoic acid;

(2R)-Cyclohexyl[(3R,4S)-3-{[3-endo-(2-ethyl-1H-benzimidazol-1-yl)-8-azabicyclo[3.2.1]oct-8-yl]methyl}-4-(3-fluorophenyl)pyrrolidin-1-yl]ethanoic acid;

1-{[(3R,4S)-3-{[3-exo-(1H-Benzimidazol-1-yl)-8-azabicyclo[3.2.1]oct-8-yl]methyl}-4-(3-fluorophenyl) pyrrolidin-1-yl]methyl}cyclohexanecarboxylic acid;

1-[((3S,4R)-3-(3-Fluorophenyl)-4-{[3-exo-(2-methyl-1H-benzimidazol-1-yl)-8-azabicyclo[3.2.1]oct-8-yl] methyl}pyrrolidin-1-yl)methyl]cyclohexanecarboxylic acid;

1-{[(3R,4S)-3-{[3-exo-(2-Ethyl-1H-benzimidazol-1-yl)-8-azabicyclo[3.2.1]oct-8yl]methyl}-4-(3-fluorophenyl) pyrrolidin-1-yl]methyl}cyclohexanecarboxylic acid;

1-{[(3R,4S)-3-{[3-endo-(1H-Benzimidazol-1-yl)-8-azabicyclo[3.2.1]oct-8-yl]methyl}-4-(3-fluorophenyl) pyrrolidin-1-yl]methyl}cyclohexanecarboxylic acid;

1-[((3S,4R)-3-(3-Fluorophenyl)-4-{[3-endo-(2-methyl-1H-benzimidazol-1-yl)-8-azabicyclo[3.2.1]oct-8-yl] methyl}pyrrolidin-1-yl)methyl]cyclohexanecarboxylic acid;

1-{[(3R,4S)-3-{[3-endo-(2-Ethyl-1H-benzimidazol-1-yl)-8-azabicyclo[3.2.1]oct-8-yl]methyl}-4-(3-fluorophenyl) pyrrolidin-1-yl]methyl}cyclohexanecarboxylic acid;

and pharmaceutically acceptable salts thereof.

Exemplary compounds of the present invention also include compounds selected from the group consisting of:

9-{[(3R,4S)-1-[(R)-carboxy(cyclohexyl)methyl]-4-(3-fluorophenyl)pyrrolidin-3-yl]methyl}-7-(2-methyl-1H-benzimidazol-1-yl)-3-oxa-9-azabicyclo[3.3.1]nonane;

9-{[(3R,4S)-1-[(R)-carboxy(cyclohexyl)methyl]-4-(3-fluorophenyl)pyrrolidin-3-yl]methyl}-7-(2-methyl-1H-benzimidazol-1-yl)-3-thia-9-azabicyclo[3.3.1]nonane;

7-(1H-benzimidazol-1-yl)-9-{[(3R,4S)-1-[(R)-carboxy (cyclohexyl)methyl]-4-(3-fluorophenyl)pyrrolidin-3-yl] methyl}-3-thia-9-azabicyclo[3.3.1]nonane;

9-{[(3R,4S)-1-[(R)-carboxy(cyclohexyl)methyl]-4-(3-fluorophenyl)pyrrolidin-3-yl]methyl}-7-(2-ethyl-1H-benzimidazol-1-yl)-3-thia-9-azabicyclo[3.3.1]nonane;

9-{[(3R,4S)-1-[(1-carboxycyclohexyl)methyl]-4-(3-fluorophenyl)pyrrolidin-3-yl]methyl}-7-(2-methyl-1H-benzimidazol-1-yl)-3-oxa-9-azabicyclo[3.3.1]nonane;

9-{[(3R,4S)-1-[(1-carboxycyclohexyl)methyl]-4-(3-fluorophenyl)pyrrolidin-3-yl]methyl}-7-(2-methyl-3H-benziidazol-3-yl)-3-thia-9-azabicyclo[3.3.1]nonane;

7-(3H-benzimidazol-3-yl)-9-{[(3R,4S)-1-[(1-carboxycyclohexyl)methyl]-4-(3-fluorophenyl) pyrrolidin-3-yl]methyl}-3-thia-9-azabicyclo[3.3.1] nonane;

9-{[(3R,4S)-1-[(1-carboxycyclohexyl)methyl]-4-(3-fluorophenyl)pyrrolidin-3-yl]methyl}-7-(2-ethyl-3H-benzimidazol-3-yl)-3-thia-9-azabicyclo[3.3.1]nonane;

and pharmaceutically acceptable salts thereof.

The subject compounds are useful in a method of modulating (e.g., inhibiting) CCR5 chemokine receptor activity in a patient in need of such modulation (inhibition) comprising the administration of an effective amount of the compound.

The present invention is directed to the use of the foregoing compounds as modulators (inhibitors) of CCR5 chemokine receptor activity.

The utility of the compounds in accordance with the present invention as modulators of CCR5 chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR5 binding. Cell lines for expressing the receptor of interest include those naturally expressing the receptor, such as EOL-3 or THP-1, or a cell engineered to express a recombinant receptor, such as CHO, RBL-2H3, HEK-293. The utility of the compounds in accordance with the present invention as inhibitors of the spread of HIV infection in cells may be demonstrated by methodology known in the art, such as the HIV quantitation assay disclosed by Nunberg, et al., *J. Virology,* 65 (9), 4887–4892 (1991).

In particular, the compounds of the following examples had activity in binding to the CCR5 receptor in the aforementioned assays, generally with an $IC_{50}$ of less than about 5 μM. Such a result is indicative of the intrinsic activity of the compounds in use as modulators of CCR5 chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, a topic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, a topic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of CCR5 chemokine receptors. Accordingly, the present invention is directed to the use of these compounds in the preparation and execution of screening assays for compounds which modulate the activity of CCR5 chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the CCR5 chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating CCR5 chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In an aspect of the present invention, a subject compound may be used in a method of inhibiting the binding of a chemokine to a CCR5 chemokine receptor of a target cell, which comprises contacting the target cell with an amount of the compound which is effective at inhibiting the binding of the chemokine to the CCR5 chemokine receptor.

The subject treated in the methods above is a mammal, preferably a human being, male or female, in whom modulation of CCR5 chemokine receptor activity is desired. "Modulation" as used herein is intended to encompass antagonism, agonism, partial antagonism, inverse agonism and/or partial agonism. In an aspect of the present invention, modulation refers to antagonism of CCR5 chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

Combined therapy to modulate CCR5 chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the antiviral agents, immunomodulators, anti-infectives, or vaccines suitable for treating HIV infection and AIDS, and known to those of ordinary skill in the art, including those listed in the following Table.

| Drug Name | Manufacturer | Indication |
|---|---|---|
| ANTIVIRALS | | |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL, HIV positive, AIDS |
| Alpha Interferon | Glaxo Wellcome | Kaposi's sarcoma, HIV, in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |

-continued

| Drug Name | Manufacturer | Indication |
| --- | --- | --- |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| mozenavir (DMP-450) | AVID (Camden, NJ) | HIV infection, AIDS, ARC (protease inhibitor) |
| EL10 | Elan Corp, PLC (Gainesville, GA) | HIV infection |
| Efavirenz (DMP 266) (-) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |

-continued

| Drug Name | Manufacturer | Indication |
|---|---|---|
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; contains lopinavir and ritonavir; Kaletra | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| Trizivir (contains abacavir, lamivudine, and zidovudine) | GlaxoSmithKline | HIV infection, AIDS, ARC (reverse transcriptase inhibitors) |
| tipranavir (PNU-140690) | Boehringer Ingelheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |

-continued

| Drug Name | Manufacturer | Indication |
| --- | --- | --- |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |

-continued

| Drug Name | Manufacturer | Indication |
| --- | --- | --- |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above just before the above Table.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-( 1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, include the following:

Ac=acetyl
Bn=benzyl
BOC or Boc=t-butyloxycarbonyl
Bu=butyl
t-Bu=tert-butyl
DIBAL=diisobutylaluminum hydride
DIEA or DIPEA=diisopropylethylamine
DIAD=diisopropylazodicarboxylate
DMF=N,N-dimethylformamide
DMSO=dimethylsulfoxide
Et=ethyl
ether=diethyl ether
h=hour(s)
HMDS=hexamethyldisilazyl
LHMDS or LiHMDS=lithium hexamethyldisilazide
Me=methyl
m=minute(s)
Ph=phenyl
Pr=propyl
i-Pr=isopropyl
PMB=p-methoxybenzyl
sat'd=saturated aqueous
rt=room temperature
TBSO=t-butyldimethylsiloxy
TEA=triethylamine
TFA=trifluoroacetic acid The compounds of the present invention can be readily prepared according to the following reaction schemes and examples, or modifications thereof. Starting materials can be made from procedures known in the art or as illustrated. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, the variables are as defined above.

SCHEME 1

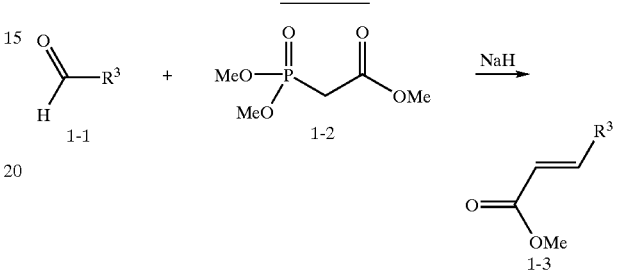

The preparation of cinnamate esters such as 1-3 (wherein $R^3$=an aromatic group) as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 or a stabilized Wittig reagent in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

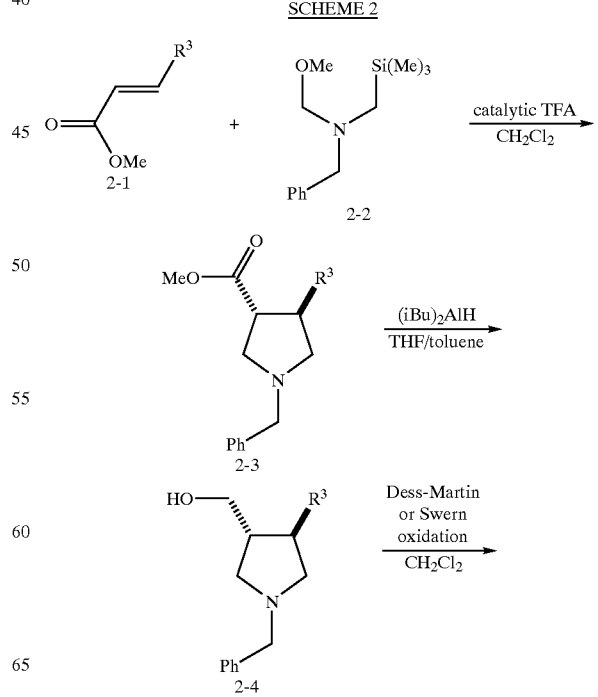

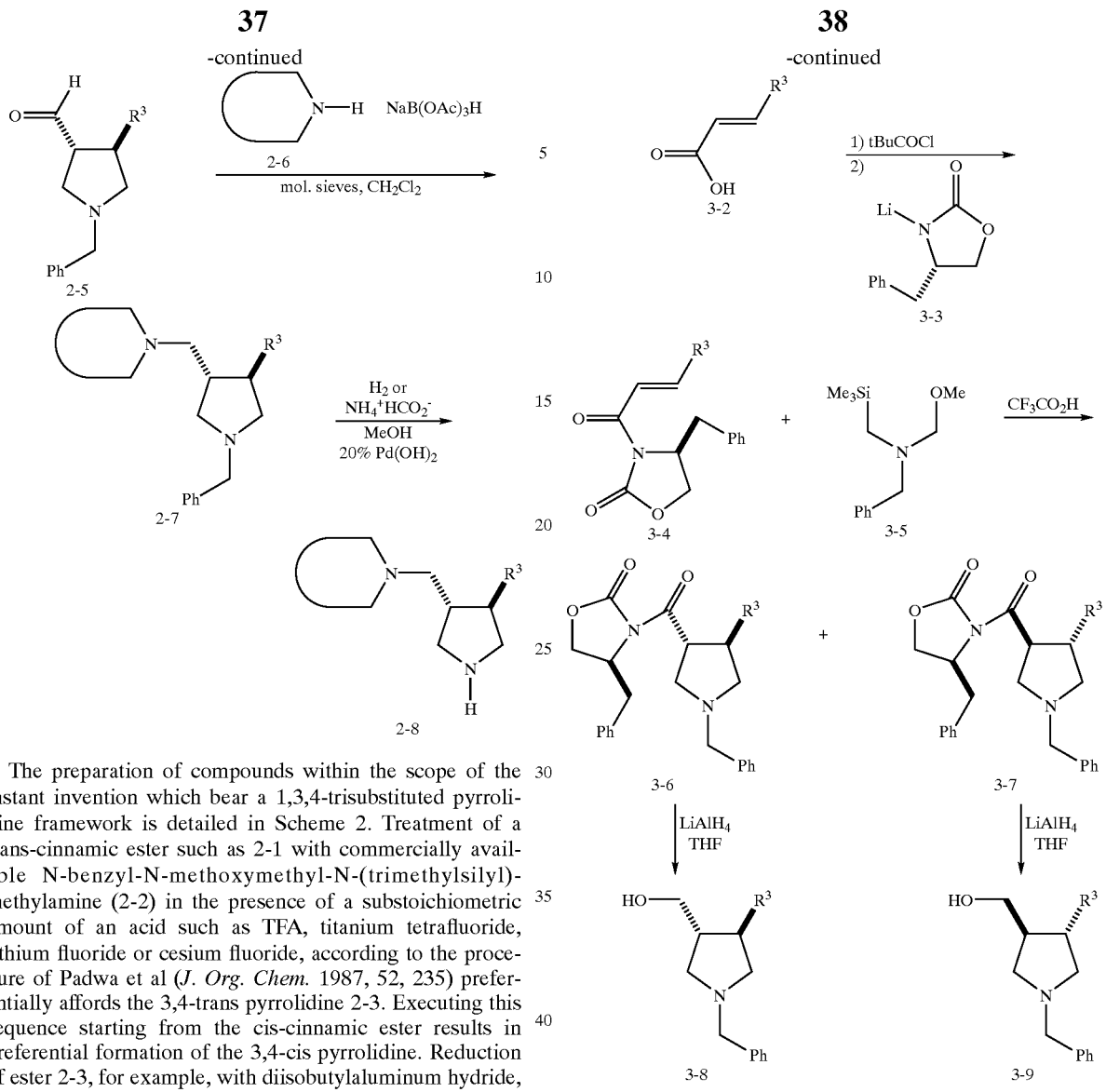

The preparation of compounds within the scope of the instant invention which bear a 1,3,4-trisubstituted pyrrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (J. Org. Chem. 1987, 52, 235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-methoxyethoxy)aluminum hydride, provides the primary alcohol 2-4. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

SCHEME 3

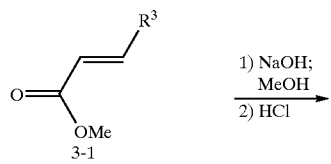

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride according to the procedure of Padwa et al (J. Org. Chem. 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumium hydride (LAH) or other strong hydride reducing agents, to provide pyrrolidines 3-8 and 3-9 in optically enriched form.

SCHEME 4

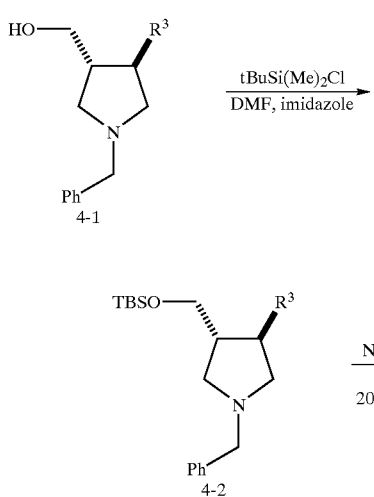

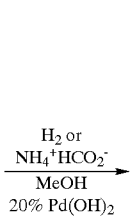

Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

SCHEME 5

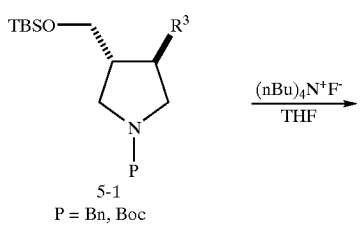

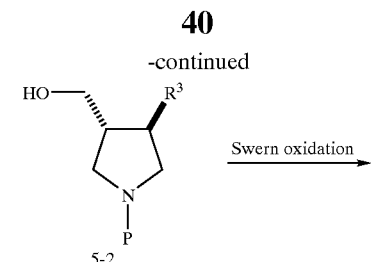

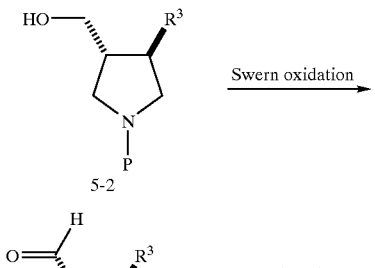

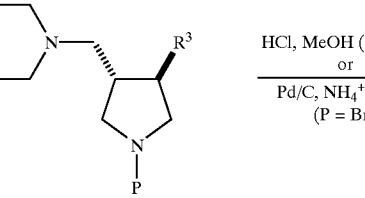

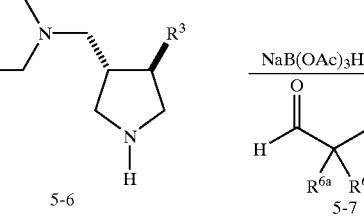

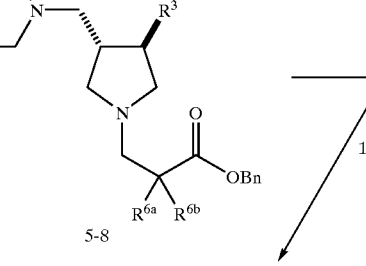

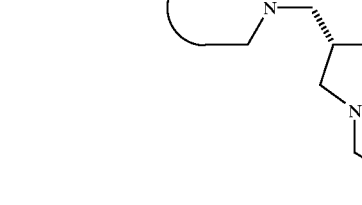

One method of preparing compounds within the scope of the instant invention is given in Scheme 5. Doubly protected pyrrolidine 5-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 5-2. Oxidation of 5-2 to 5-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-4 then provides diamine 5-5. Deprotection of the pyrrolidine nitrogen, when P=Boc, can be carried out with HCl in methanol or with trifluoroacetic acid and anisole in dichloromethane, to give secondary amine 5-6. When P=benzyl, debenzylation is carried out in the presence of palladium on carbon as a catalyst, using either hydrogen gas or ammonium formate to effect transfer hydrogenation. Reductive amination with formyl ester 5-7 then provides pyrrolidine 5-8. Removal of the benzyl group can be carried out under standard reductive conditions, for example, hydrogen gas in the presence of a supported or unsupported palladium catalyst, to afford acid 5-9. Alternatively, if a 4-methoxybenzyl ester is utilized in place of the benzyl ester of compound 5-7, then the final deprotection can be carried out under acid conditions, for example, formic acid at 55° C. This latter approach is useful if the parent molecule contains functionality sensitive to catalytic hydrogenation.

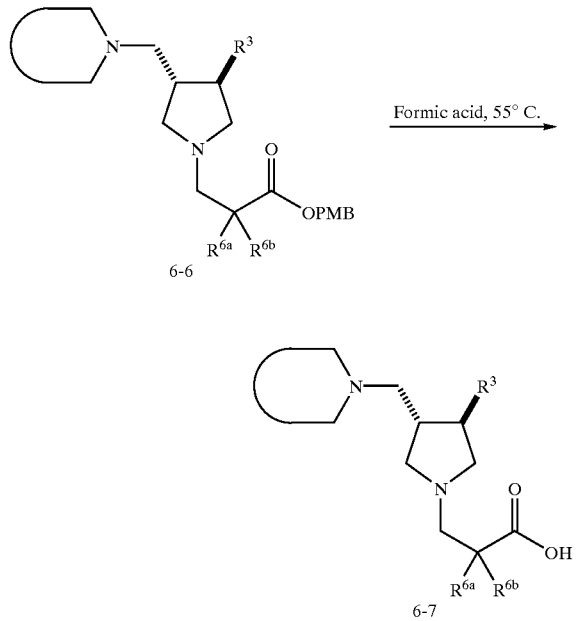

Another method for preparing compounds in the instant invention is shown in Scheme 6. Reductive amination of pyrrolidine 4-3 with aldehyde ester 6-1 affords pyrrolidine 6-2. Removal of the silyl protecting group with tetrabutylammonium fluoride provides alcohol 6-3, which can be oxidized under standard conditions, for example the Swern oxidation, to give aldehyde 6-4. Reductive amination of 6-4 with a suitable secondary amine 6-5 yields ester 6-6 which can be deprotected under acidic conditions, for example, with formic acid, to afford compound 6-7.

SCHEME 6

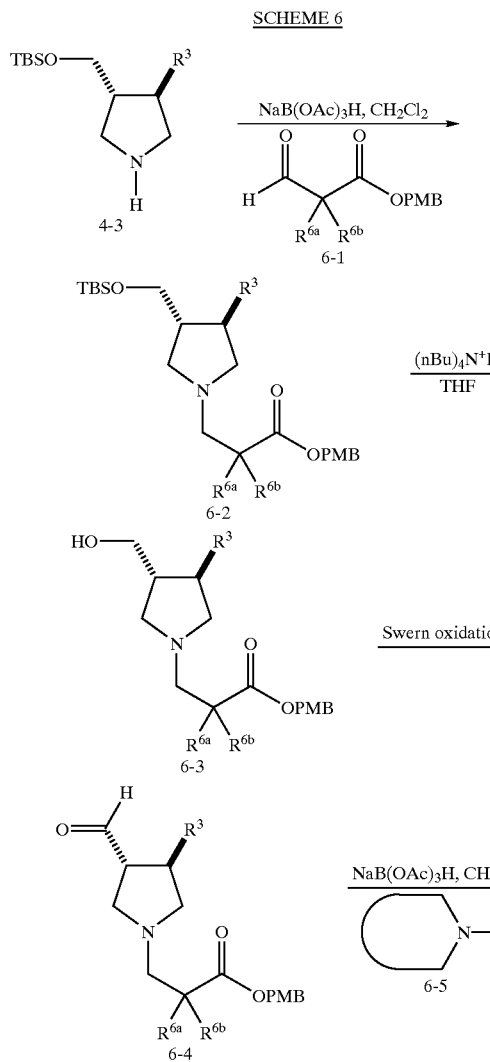

SCHEME 7

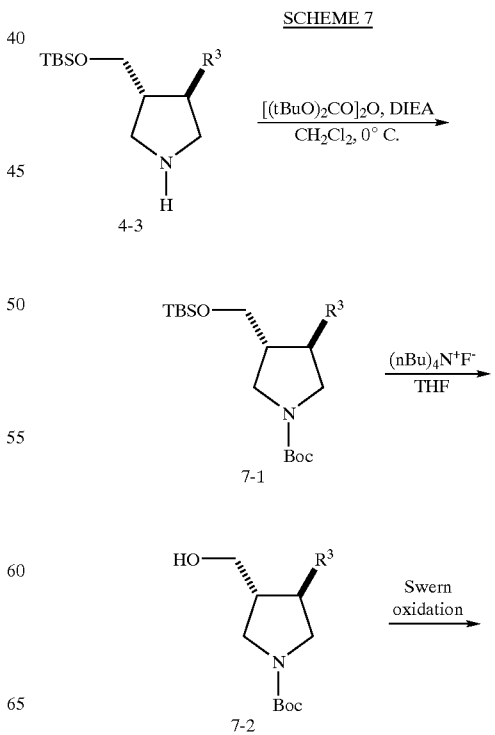

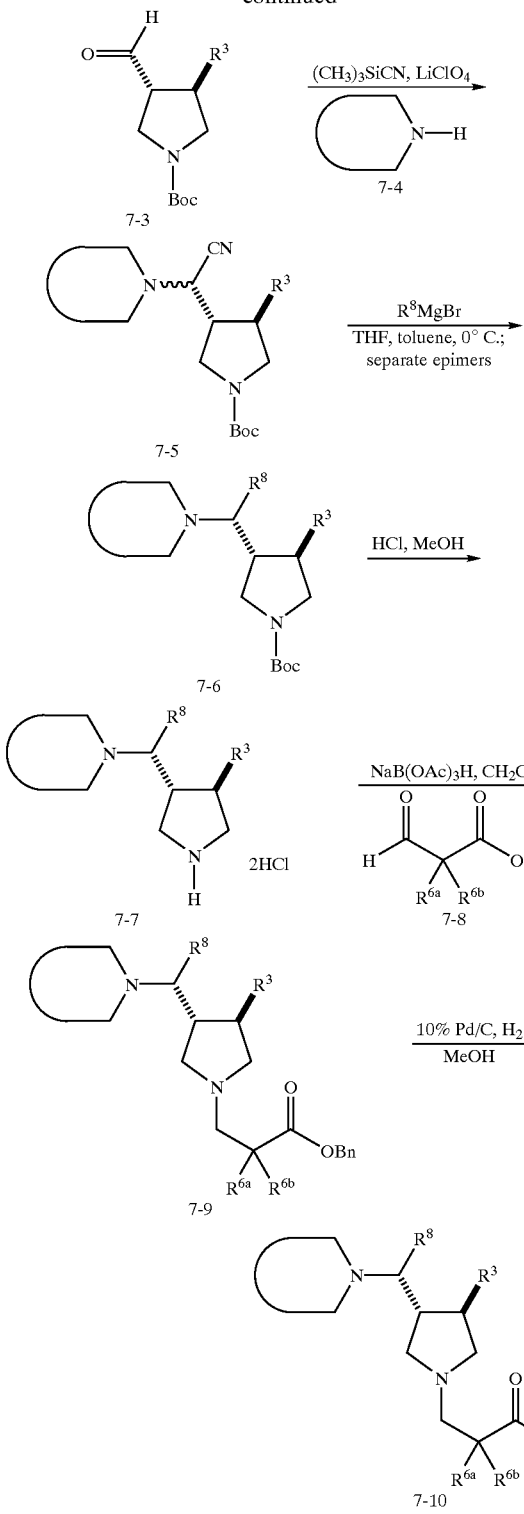

hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Treatment of 7-3 with a secondary amine 7-4, and trimethylsilyl cyanide in the presence of lithium perchlorate affords cyanoamine 7-5. Treatment of 7-5 with a suitable organomagnesium reagent $R^8MgBr$ yields the branched compound 7-6. The diastereomers formed in this process can be separated at this stage, or at any point later in the synthesis by standard methods, including fractional crystallization, column chromatography, flash chromatography, high pressure liquid chromatograghy (HPLC) or medium pressure liquid chromatography (MPLC), optionally by use of a stationary phase derivatized with chiral, non-racemic groups to enable separation of enantiomers and to enhance separation of isomeric mixtures. The Boc group of 7-6 can be removed under acidic conditions, for example hydrochloric acid in methanol, to afford secondary pyrrolidine 7-7. Reductive amination with aldehyde 7-8 under mild conditions, for example with sodium cyanoborohydride in methylene chloride, provides ester 7-9. Removal of the benzyl protecting group by catalytic reduction then affords compound 7-10.

SCHEME 8

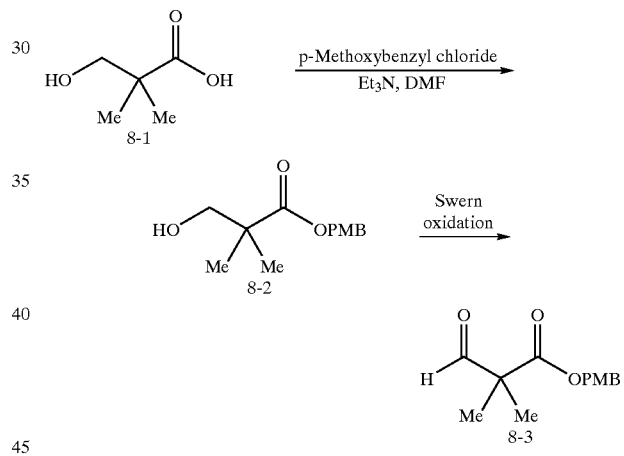

Synthesis of aldehyde esters such as 6-1 and 7-8 can be carried out by a number of routes, one of which is shown in Scheme 8. The available hydroxy acid 8-1 is esterified with a suitable protecting group (such as a para-methoxybenzyl group) in the presence of a suitable base (such as triethylamine or DIEA), to give ester 8-2. Oxidation of 8-2, for example by Swern oxidation, then affords aldehyde 8-3.

A method for preparing compounds in the instant invention wherein an additional substituent $R^8$ is present is given in Scheme 7. Protection of pyrrolidine 4-3 with Boc anhydride under standard conditions provides doubly protected pyrrolidine 7-1, which can be desilylated by exposure to tetrabutylammonium fluoride in THF, affording 7-2. Oxidation of 7-2 to aldehyde 7-3 is carried out using Swern's oxidation conditions. Other methods for oxidizing a primary

SCHEME 9

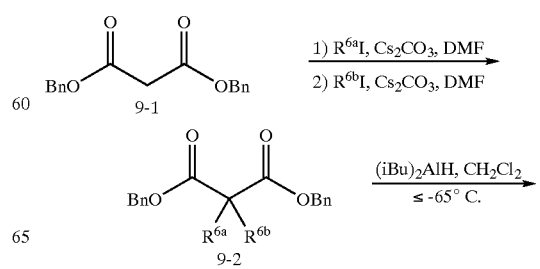

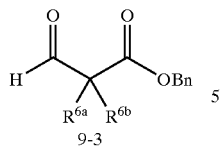

Synthesis of aldehyde ester 6-1 where the $R^6$ substituents are distinct or identical can be accomplished as shown in Scheme 9. Alkylation of dibenzyl malonate with a suitable alkylating agent, such as an alkyl iodide, bromide, toluenesufonate and the like, in the presence of a base such as cesium carbonate, potassium carbonate, or other agents of moderate basicity, followed by repetition of the procedure with a second alkyl halide or alkyl toluenesulfonate, provides dialkylated product 9-2. Treatment of diester 9-2 with di-isobutylaluminum hydride at low temperature affords ester aldehyde 9-3.

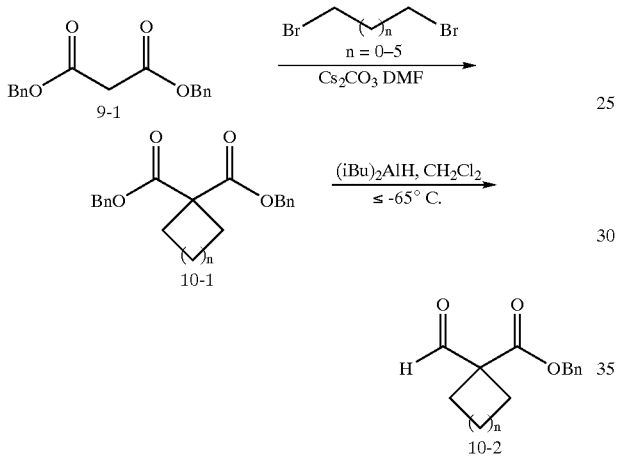

Synthesis of aldehyde ester 6-1 where the $R^{6a}$ and $R^{6b}$ form a ring substituents can be accomplished as shown in Scheme 10. Dialkylation of dibenzyl malonate with a suitable dialkylating agent, such as an alkyl diiodide, dibromide, ditoluenesufonate and the like, in the presence of a base such as cesium carbonate, potassium carbonate, or other agents of moderate basicity, provides cyclic derivative 10-1. Treatment of diester 10-1 with di-isobutylaluminum hydride at low temperature affords ester aldehyde 10-2. An analogous scheme can be used for cyclic derivatives containing a heteroatom in the ring by selection of the appropriate precursor.

SCHEME 11

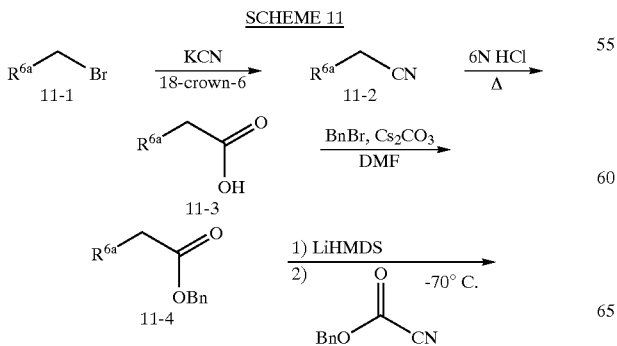

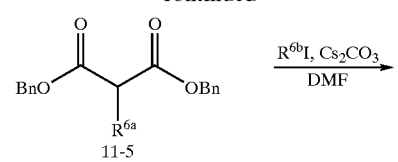
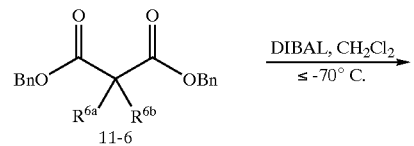
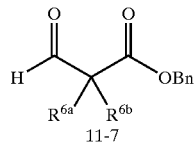

An alternative synthesis of aldehyde ester intermediates is given in Scheme 11. Treatment of a commercially available alkyl methyl bromide with potassium cyanide in the presence of 18-crown-6 provides nitrile 11-2. Hydrolysis under acidic conditions affords acid 11-3. Esterification with benzyl bromide in the presence of cesium carbonate in DMP yields ester 11-4. Deprotonation of ester 11-4 with a strong, non-nucleophilic base, such as lithium hexamethyldisilazide, followed by treatment with benzyl cyanoformate, provides diester 11-5, which can be alkylated with a suitably activated haloalkyl group to provide dialkylated product 11-6. Reduction with DIBAL at low temperature then provides the desired intermediate 11-7.

SCHEME 12

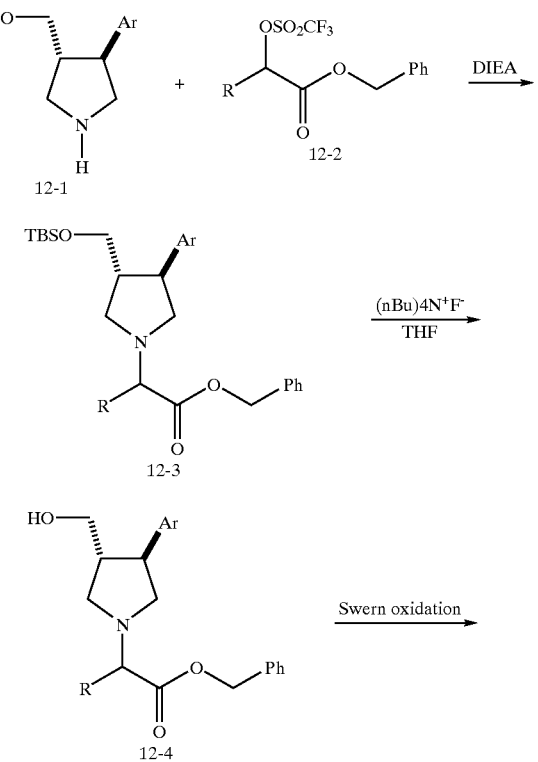

-continued

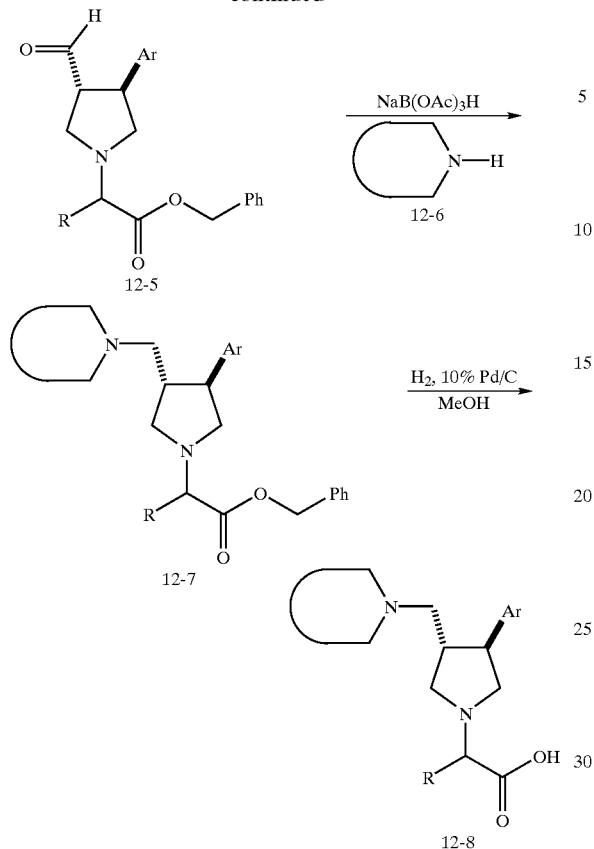

Alternatively, the benzyl ester can be cleaved by treatment with strong aqueous base if the remainder of the molecule is stable to those conditions.

SCHEME 13

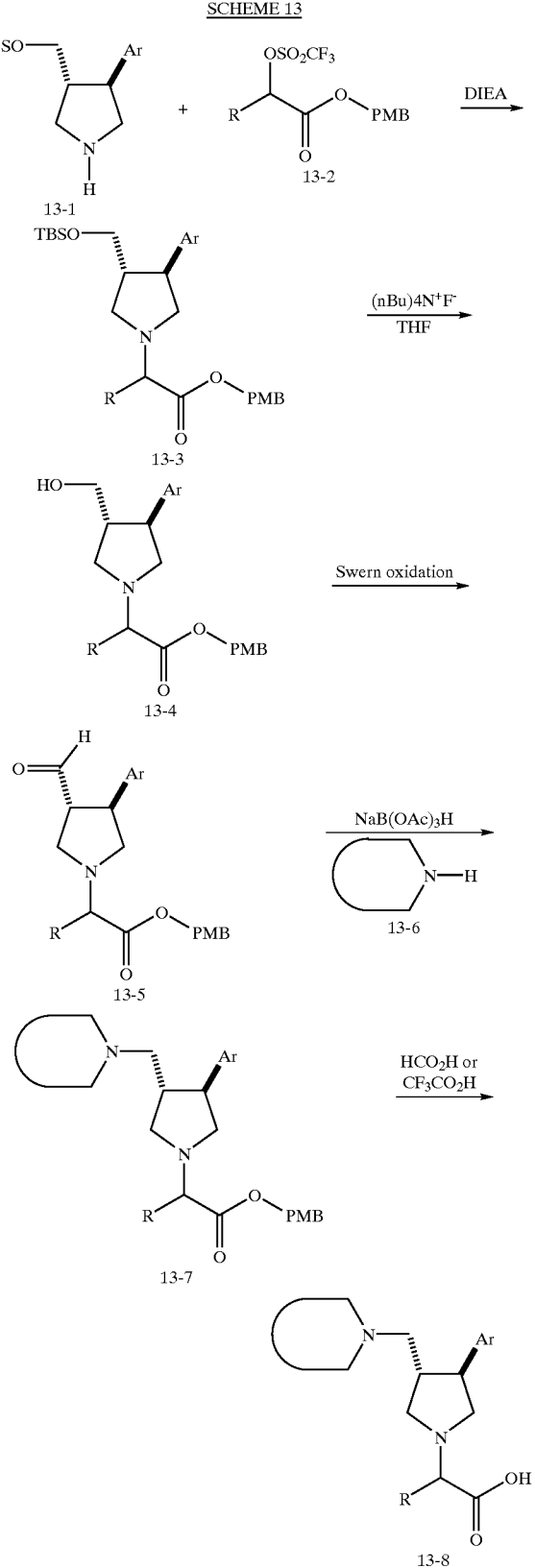

Preparation of some 1,3,4-trisubstituted pyrrolidines within the scope of the instant invention is given in Scheme 12. Alkylation of pyrrolidine 12-1 with the trifluoromethanesulfonate (triflate) ester of a suitable alpha-hydroxy ester derivative 12-2 in the presence of a hindered base such as DIEA ((N,N-(diisopropyl)ethylamine) or a sparingly soluble base such as potassium carbonate provides the N-substituted product 12-3. Triflate ester 12-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 12-2 instead of a triflate, such as chloride, bromide, iodide, methanesulfonate, p-toluenesulfonate, etc. Deprotection of silyl ether 12-3 is carried out with tetrabutylammonium fluoride in THF, to afford alcohol 12-4. Alternatively, acidic conditions can be used to remove the silyl group, for example aqueous trifluoroacetic acid, hydrogen fluoride in pyridine, hydrochloric acid, etc. Oxidation of 12-4 to the aldehyde 12-5 is accomplished using the Swern oxidation conditions.

Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 12-6 then provides diamine 12-7, which can itself be a chemokine receptor antagonist. Cleavage of the benzyl group with catalytic hydrogenation, for example under an atmosphere of hydrogen in the presence of 10% palladium on carbon as catalyst in methanol or ethanol as solvent, provides acid 12-8.

Preparation of 1,3,4-trisubstituted pyrrolidines within the scope of the instant invention wherein the carboxylic acid protecting group is cleavable under mild acidic conditions is given in Scheme 6. Alkylation of pyrrolidine 13-1 with the triflate ester of a suitable alpha-hydroxy ester derivative 13-2 in the presence of a hindered base such as DIEA or a sparingly soluble base such as potassium carbonate provides the N-substituted product 13-3 (PMB=para-methoxybenzyl). Triflate ester 13-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 13-2 instead of a triflate, such as chloride, bromide, iodide, methanesulfonate, p-toluenesulfonate, etc. Deprotection of silyl ether 13-3 is carried out with tetrabutylammonium fluoride in THF, to afford alcohol 13-4. Alternatively, mildly acidic conditions in some cases can be used to selectively remove the silyl group, for example aqueous trifluoroacetic acid, hydrogen fluoride in pyridine, hydrochloric acid, etc. Oxidation of 13-4 to the aldehyde 13-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 13-6 then provides diamine 13-7, which can itself be a chemokine receptor antagonist. Cleavage of the PMB group with acid, for example with formic acid or trifluoroacetic acid plus anisole, provides acid 13-8. Alternatively, the ester can be cleaved by treatment with strong aqueous base or by catalytic hydrogenation if the remainder of the molecule is stable to those conditions.

SCHEME 14

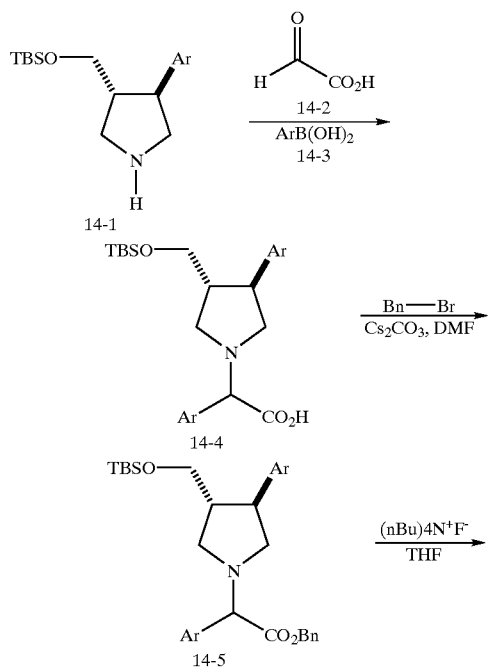

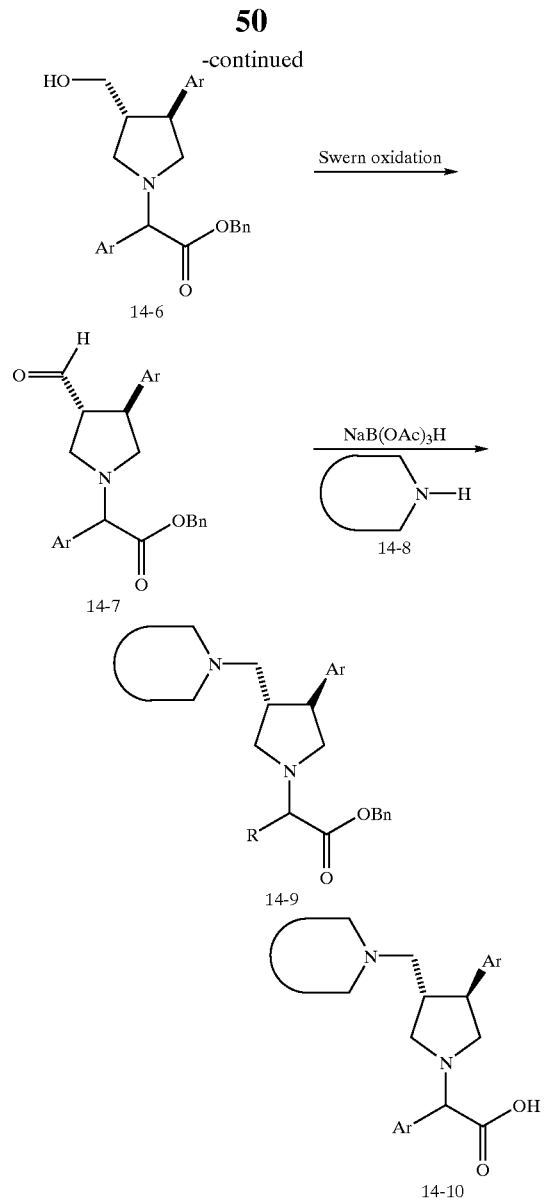

An alternative route for the synthesis of pyrrolidines with a 1-(α-arylacetic acid) substituent is given in Scheme 14. Reaction of the protected pyrrolidine 14-1 with glyoxylic acid in the presence of an aryl boronic acid 14-3 provides the N-aralkylated product 14-4 (see Petasis, N. A.; Goodman, A.; Zavialov, I. A. Tetrahedron 1997, 53, 16463–16470; and PCT Int. Appl. WO 9800398). Protection of the acid by alkylation with benzyl bromide in DMF in the presence of cesium carbonate provides ester 14-5. Deprotection of the silyl group with tetrabutylammonium fluoride in TBF, or with mild acid such as aqueous trifluoroacetic acid, then provides alcohol 14-6. Alternatively, simultaneous removal of the silyl group of 14-4 and formation of the ester can be carried out by heating 14-4 in an anhydrous solution of the esterifying alcohol in the presence of acid, such as toluenesulfonic acid, triflic acid, hydrochloric acid, and the like. The alcohol 14-6 is oxidized to aldehyde 14-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp.

1167–1171 (1992)). Reductive amination with cyclic amine 14-8 then provides diamine 14-9, which can itself be a chemokine receptor antagonist. Deprotection of the benzyl ester is carried out with catalytic hydrogenation, for example under an atmosphere of hydrogen in the presence of 10% palladium on carbon as catalyst in methanol or ethanol as solvent, provides acid 14-10. Alternatively, the benzyl ester can be cleaved by treatment with strong aqueous base if the remainder of the molecule is stable to those conditions.

Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 15-2. Oxidation of 15-2 to 15-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 15-4 then provides diamine 15-5, which can itself be a chemokine receptor antagonist. Deprotection of the pyrrolidine nitrogen, when P=Boc, can be carried out with HCl in methanol or with trifluoroacetic acid and anisole in dichloromethane, to give secondary amine 15-6. When P=benzyl, debenzylation is carried out in the presence of palladium on carbon as a catalyst, using either hydrogen gas or ammonium formate to effect transfer hydrogenation. Reductive amination with keto-acid 15-7 then provides pyrrolidine 15-8.

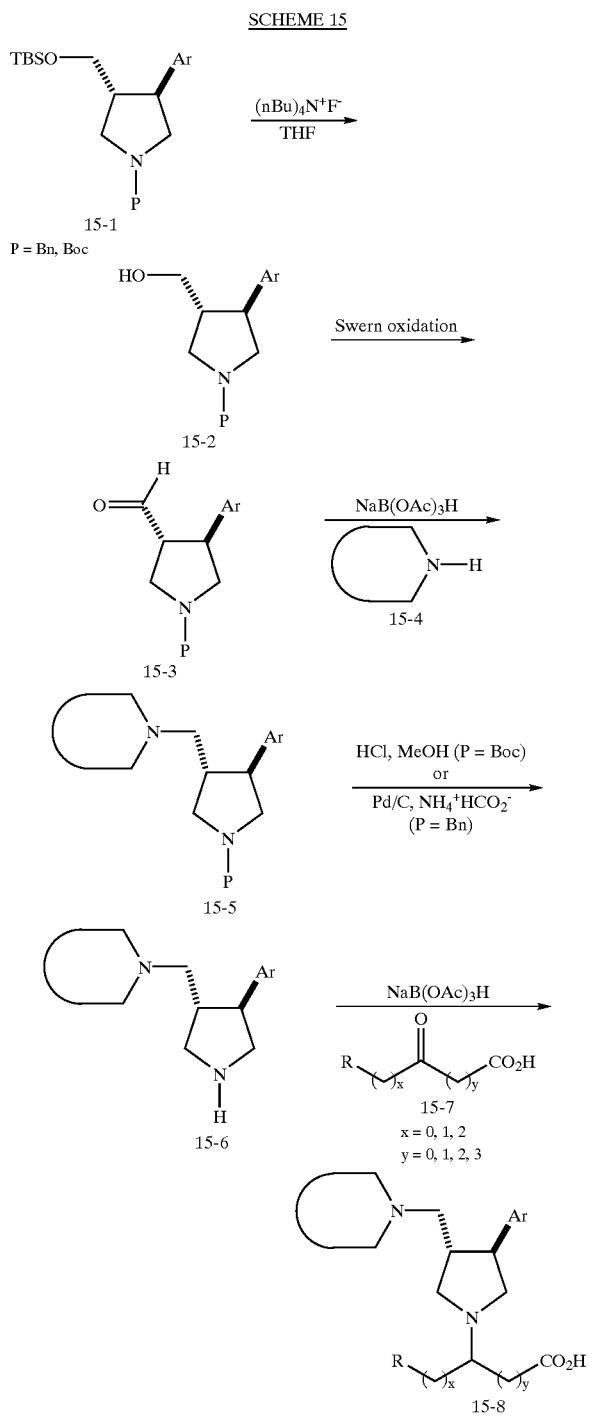

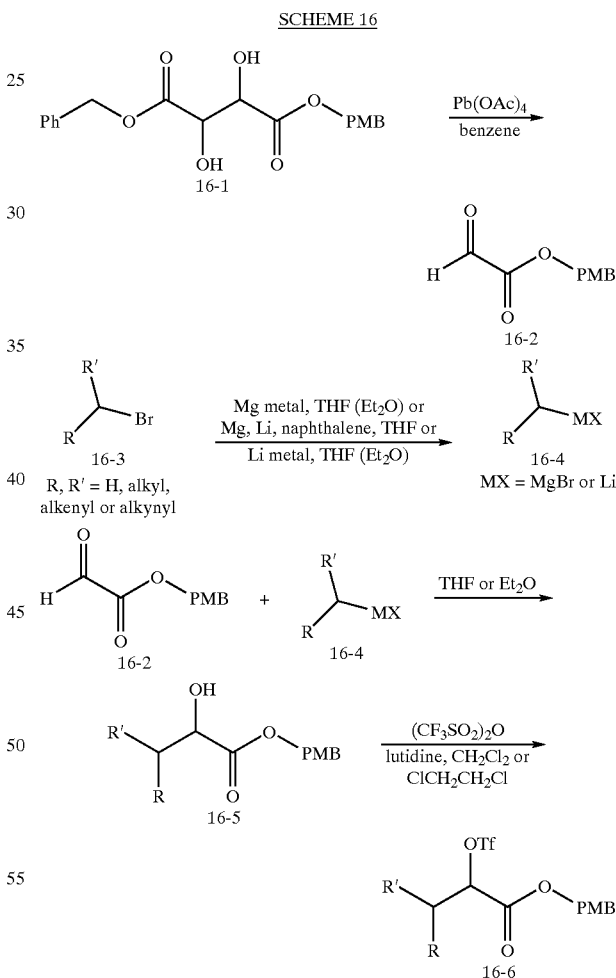

Another method of preparing compounds within the scope of the instant invention is given in Scheme 15. Doubly protected pyrrolidine 15-1 (obtained either as shown in Scheme 16 illustrates preparation of intermediate 2-alkyl-2-trifluoromethanesulfonoxyacetic acid derivatives when the 1-alkyl-1-hydroxyacetic acid is not commercially available. Treatment of the para-methoxybenzyl ester of tartaric acid with lead tetraacetate in benzene provides the glyoxylic ester 16-2. Separately, a commercially available alkyl bromide (such as cyclobutylmethyl bromide) is treated with magnesium metal (in the absence or presence of lithium/naphthalene) or with lithium metal to provide the organometallic intermediate 16-4. Adding 16-4 to the aldehyde 16-2 provides the 2-hydroxy-ester 16-5. Formation of the trifluoromethanesulfonate ester is carried out under standard conditions (for example, with trifluoromethansulfonic anhydride in the presence of a hindered base such as 2,6-lutidine or DIEA in a halogenated solvent at between −78 degrees C. to room temperature, preferably near 0 degrees C., to give 16-6, which is then employed as described above.

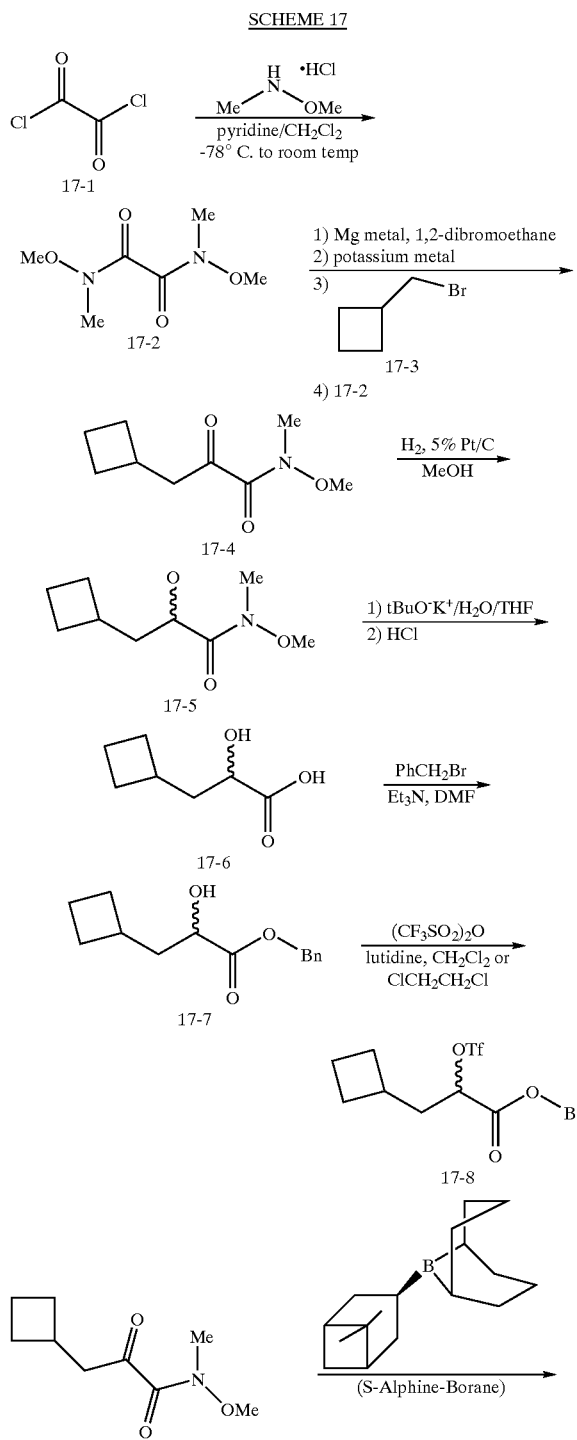

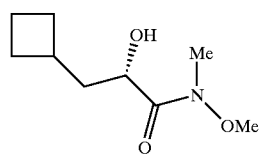

Scheme 17 illustrates an alternate preparation of intermediate 2-alkyl-2-trifluoromethanesulfonoxyacetic acid derivatives; in this example, the side chain is exemplified by a cyclobutylmethyl subunit. Treatment of oxalyl chloride (17-1) with N-methyl-N-methoxyamine hydrochloride in the presence of pyridine yields the bis amide 17-2 (also called the bis-Weinreb amide). In a separate vessel, formation of magnesium dibromide in TIF, followed by addition of potassium metal, forms a very reactive grade of magnesium metal. Addition of a suitable aliphatic bromide or iodide, for example cyclobutylmethyl bromide (17-3), provides the desired organomagnesium reagent in situ. Addition of bis-amide 17-2, followed by suitable workup, affords the keto-ester 17-4. This compound is reduced by hydrogenation in the presence of 5% platinum on carbon and triethylamine to the racemic alcohol 17-5. Hydrolysis with potassium t-butoxide in TBF/water followed by acidification yields the hydroxy acid 17-6. Acid 17-6 is then protected, for example as the benzyl ester, by treatment with benzyl bromide and triethylamine in DMF, to provide 17-7. This ester is then activated with triflic anhydride (or other triflating agents) under the usual conditions. Alternatively, keto-ester 17-4 can be reduced enantioselectively, for example with B-isopinocampheyl-9-borabicyclo[3.3.1]nonane (also known as S-Alpine-borane®) to provide S-hydroxy derivative 17-9, which can be carried through the rest of the sequence as for 17-5.

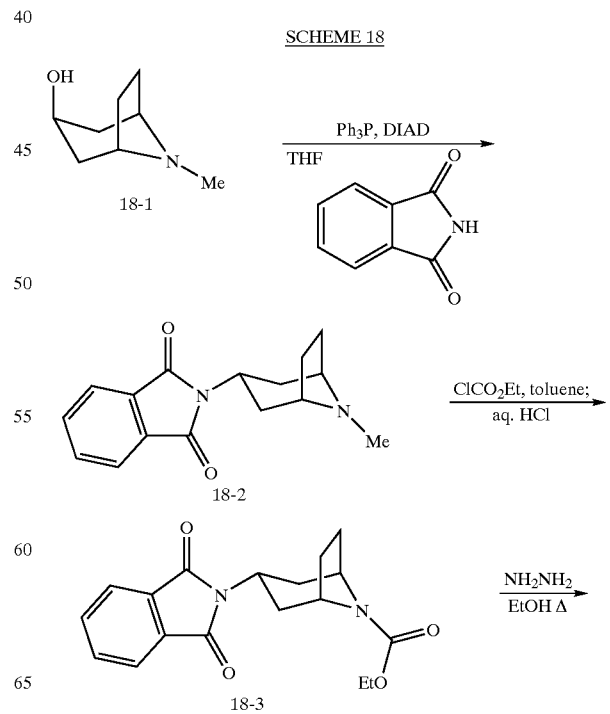

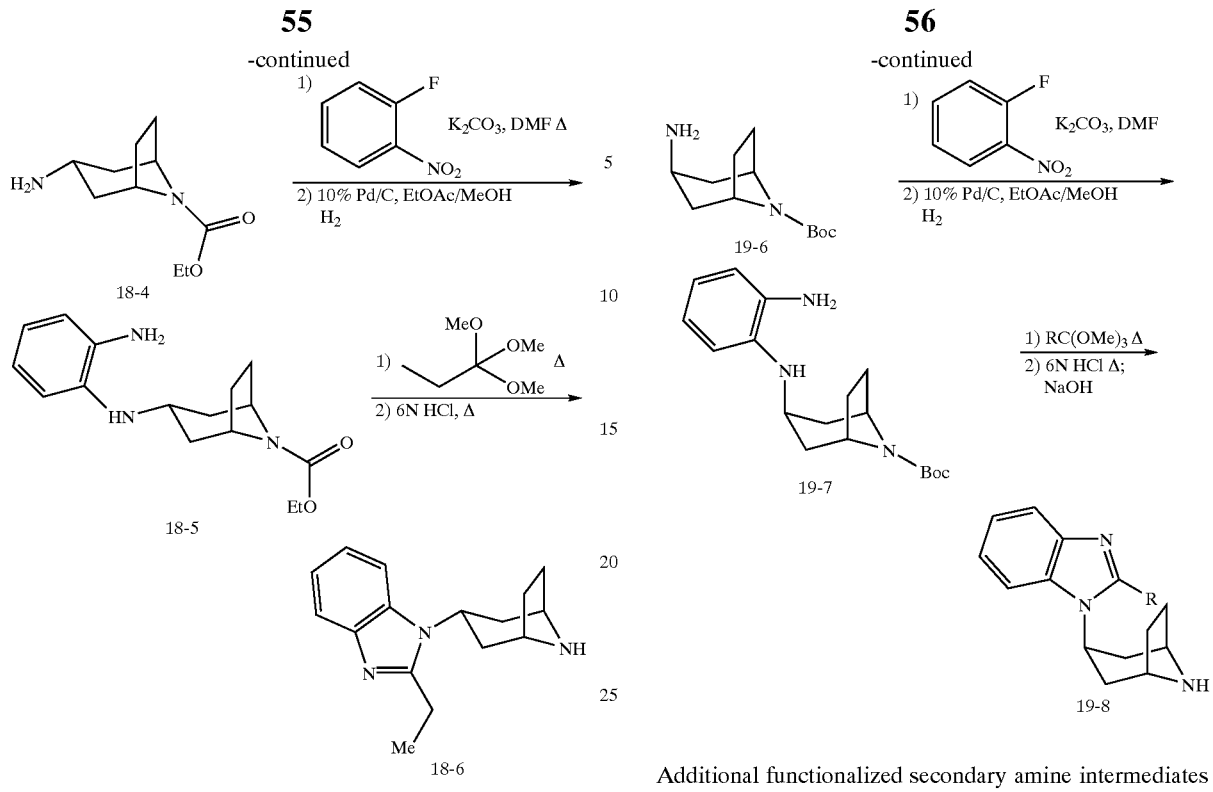

Functionalized piperidine intermediates for the instant invention can be prepared as shown in Scheme 18. Treatment of tropine with phthalimide, triphenylphosphine and diisopropylazodicarboxylate affords the phthalimide adduct 18-2. Demethylation/acylation can be carried out with ethyl chloroformate in warm toluene, to provide carbamate 18-3, which upon treatment with hydrazine in ethanol at reflux affords primary amine 18-4. Addition of 2-fluoronitrobenzene in refluxing DMF yields the corresponding aryl adduct, which after catalytic hydrogenation provides aniline 18-5. Refluxing the latter with a suitable orthoester derivative, for example trimethyl-orthopropionate, followed by heating with aqueous hydrochloric acid then provides the desired intermediate 18-6.

SCHEME 19

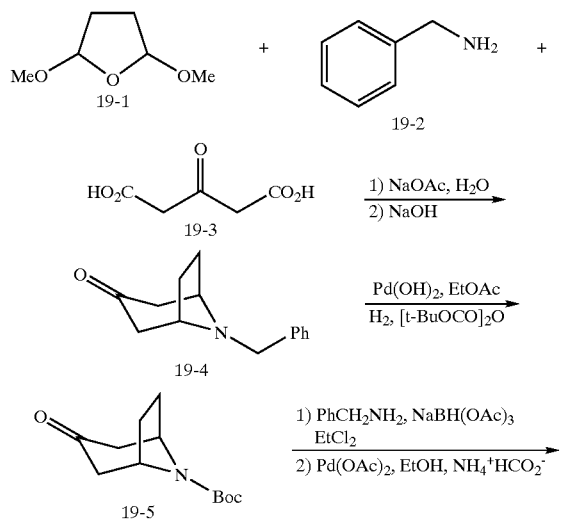

Additional functionalized secondary amine intermediates for the instant invention can be prepared as shown in Scheme 19. Combination of reagents 19-1, 19-2 and 19-3 in the presence of sodium acetate under mild aqueous conditions affords tropone 19-4, which upon catalytic hydrogenation in the presence of di-t-butyl dicarbonate affords the Boc protected tropane 19-5. Reductive amination with benzylamine, followed by removal of the benzyl group by catalytic hydrogenation affords endo-amine 19-6. Treatment of the latter with 2-fluoronitrobenzene in refluxing DMF in the presence of potassium carbonate yields the aryl adduct, whose nitro group can then be reduced under standard conditions to provide the aniline 19-7. Refluxing with an appropriate alkyl orthoformate derivative, followed by heating with 6N hydrochloric acid, then affords the desired intermediate 19-8.

The following examples serve only to illustrate the invention and its practice. The examples are not to be construed as limitations on the scope or spirit of the invention.

General Considerations

Concentration of solutions was carried out on a rotary evaporator under reduced pressure. Flash chromatography (FC) was carried out on silica gel (230–400 mesh). NMR spectra were obtained in $CDCl_3$ solution unless otherwise noted. Coupling constants (J) are in hertz (Hz).

HPLC Conditions

HPLC A. Retention time using the following conditions: Column: YMC ODS A, 5μ, 4.6×50 mm; Gradient Eluant: 10:90 to 90:10 v/v $CH_3CN/H_2O$+0.5% TFA over 4.5 min, hold 30 sec; Detection: PDA, 210–400 nm; Flow Rate: 2.5 mL/min.

Pyrrolidine 1

3-(R)-(t-Butyldimethylsilyloxymethyl)-4-(S)-phenyl pyrrolidine

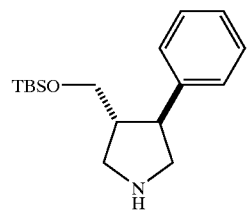

Step A: 3-((E)-Cinnamoyl)-4-(S)-benzyl oxazolidin-2-one

A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C., then cooled to −78° C. In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to rt and was stirred for 20 h. The reaction was quenched with 300 mL of sat'd NH$_4$Cl; the resulting mixture was partitioned between EtOAc and H$_2$O and the layers were separated. The organic layer was dried over MgSO$_4$. The aqueous layer was extracted with 2×EtOAc; the extracts were dried and all of the organic extracts were combined. Partial concentration in vacuo caused precipitation of a solid; the mixture was diluted with hexanes and allowed to stand at rt for 1.5 h. The precipitate was filtered and dried to afford the title compound: $^1$H NMR (500 MHz, CDCl$_3$) δ2.86 (dd, J=13.5, 9.5, 1H), (3.38, J=13.5, 3.5, 1H), 4.20–4.27 (m, 2H), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-carbonyl)-4-(S)-benzyl oxazolidin-2-one and 3-(1-benzyl-4-(R)-phenyl-pyrrolidine-3-(S)-carbonyl)-4-(S)-benzyl oxazolidin-2-one A solution of 402 g (1.3 mol) of 3-((E)-cinnamoyl)-4-(S)-benzyl oxazolidin-2-one (from Step A) and 474 g (2.0 mol) of N-methoxymethyl-N-trimethylsilylmethyl benzyl amine in 4 L of CH$_2$Cl$_2$ at −10° C. was treated with 6 mL of trifluoroacetic acid. The resulting mixture was stirred cold for 4 h and then was treated with an additional 4 mL of trifluoroacetic acid. The reaction mixture was warmed to rt and stirred for 20 h. The reaction was quenched with 2 L of sat'd NaHCO$_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 3-(1-benzyl-4-(S)-phenylpyrrolidine-3-(R)-carbonyl)-4-(S)-benzyl oxazolidin-2-one and 3-(1-benzyl-4-(R)-phenylpyrrolidine-3-(S)-carbonyl)-4-(S)-benzyl oxazolidin-2-one. For 3-(1-benzyl-4-(S)-phenylpyrrolidine-3-(R)-carbonyl)-4-(S)-benzyl oxazolidin-2-one: $^1$H NMR (500 MHz) δ2.66 (t, J=8.0, 1H), 2.78 (dd, J=13.0, 9.0, 1H), 2.87 (dd, J=9.0, 4.5, 1H), 3.21–3.27 (m, 2H), 3.64 (d, J=11.5, 1H), 3.77 (d, J=11.5, 1H), 4.10–4.15 (m, 2H), 4.61–4.65 (m, 1H), 7.16–7.38 (15H). For 3-(1-benzyl-4-(R)-phenylpyrrolidine-3-(S)-carbonyl)-4-(S)-benzyl oxazolidin-2-one: $^1$H NMR (500 MHz, CDCl$_3$) δ2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.07–4.12 (m, 2H), 4.16 (t, J=9.0, 1H), 4.26–4.30 (m, 1H), 4.65–4.69 (m, 1H), 7.03–7.40 (15H).

Step C: 1-Benzyl-3-(R)-hydroxymethyl-4-(S)-phenylpyrrolidine

A solution of 3-(1-benzyl-4-(S)-phenylpyrrolidine-3-(R)-carbonyl)-4-(S)-benzyl oxazolidin-2-one (from Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mmL of H$_2$O, then 40 mL of 2.0 N NaOH, then 115 mL of H$_2$O and then was stirred at rt for 1.5 h. The mixture was filtered and the filtrate was concentrated. Chromatography on 4 kg of silica using 4:1 hexanes/acetone (14 L), then 7:3 hexanes/acetone as the eluant afforded the title compound: $^1$H NMR (400 MHz, CDCl$_3$) δ2.38–2.46 (m, 2H), 2.78–2.88 (3H), 3.20–3.26 (2H), 3.65 (dd, J=12.0, 4.0 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(t-butyldimethylsilyloxymethyl)-4-(S)-phenyl pyrrolidine A solution of 82.0 g (0.31 mol) of 1-benzyl-3-(R)-hydroxymethyl-4-(S)-phenyl pyrrolidine (from Step C) and 46.5 g (0.36 mol) of N,N-diisopropylethylamine in 1 L of CH$_2$Cl$_2$ was treated with 54.2 g (0.36 mol) of t-butyldimethylsilyl chloride and the resulting mixture was stirred at rt for 20 h. The reaction was quenched with 750 mL of sat'd NaHCO$_3$ and the layers were separated. The organic layer was combined with 150 g of silica gel and aged for 45 min. The mixture was filtered and the filtrate was concentrated to afford the title compound.

Step E: 3-(R)-(t-Butyldimethylsilyloxymethyl)-4-(S)-phenylpyrrolidine

A mixture of 117 g (0.31 mol) of 1-benzyl-3-(R)-(t-butyldimethylsilyloxymethyl)-4-(S)-phenyl pyrrolidine (from Step D), 31.5 g (0.50 mol) ammonium formate, 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of CH$_2$Cl$_2$, washed with 300 mL of 10% NH4OH solution, 200 mL of sat'd NaCl, dried over MgSO4 and concentrated to afford the title compound: $^1$H NMR (400 MHz, CDCl$_3$) δ0.09 (s, 3H), −0.08 (s, 3H), 0.77 (s, 9H), 2.25–2.30 (m, 1H), 2.84–2.96 (4H), 3.18 (dd, J=11.2, 3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

Pyrrolidine 2

3-(R)-(t-Butyldimethylsilyloxymethyl)-4-(S)-(3-fluoro)phenylpyrrolidine

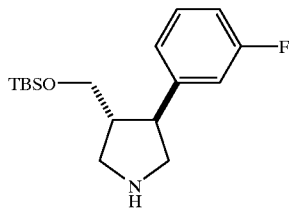

The title compound was prepared using procedures analogous to those described to prepare Pyrrolidine 1, except that trans-(3-fluoro)cinnamic acid was substituted for trans-cinnamic acid in Step A. For the title compound: $^1$H NMR (400 MHz, CDCl$_3$): δ0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 1H), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1H); ESI-MS 310 (M+H); HPLC A: 3.05 min.

Aldehyde 1

Benzyl (2R)-cyclohexyl[(3S,4R)-3-(3-fluorophenyl)-4-formylpyrrolidin-1-yl]ethanoate

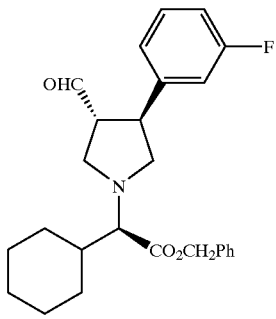

Step A: 2-(S)-Hydroxy-2-(cyclohexyl)acetic acid, benzyl ester

A flask was charged with (S)-hexahydromandelic acid (0.88 g, 5.56 mmol), Bu$_4$NI (0.4 g, 1.1 mmol) and KOH (11.1 mL, 5.56 mmol, 0.5 M in water). 11 mL of chloroform was added followed by benzyl bromide (0.66 mL, 5.56 mmol). The mixture was refluxed for 5 h then cooled and diluted with 100 ml CH$_2$Cl$_2$. The layers were separated and the organic was dried and concentrated. Flash Chromatography (7/1 hexane/EtOAc) gave the desired product. R$_F$: 0.37 (4:1 v/v hexanes/EtOAc); $^1$H NMR (300 MHz, CDCl$_3$) δ1.11–1.38 (m, 11H), 2.65 (d, J=6.3 Hz, 1H), 4.06 (dd, J=6.3, 3.5 Hz, 1H), 5.22 (s, 2H), 7.30–7.39 (m, 5H).

Step B: Benzyl (2S)-cyclohexyl{[(trifluoromethyl)sulfonyl]oxy}ethanoate

A solution of trifluoromethanesulfonic anhydride (12.7 g, 45.2 mmol) in 40 mL CH$_2$Cl$_2$ was cooled in an ice bath. A solution of 2-(S)-hydroxy-2-(cyclohexyl)acetic acid, benzyl ester (10.7 g, 43 mmol, from Step A) and 2,6-lutidine (4.6 g, 43 mmol) in 40 mL CH$_2$Cl$_2$ was added dropwise over 25 min and the mixture was stirred for an additional 20 min. The mixture was washed with water and sat'd NaCl then the organic layer was dried over sodium sulfate and concentrated. Flash chromatography (150 g silica, 0→15% EtOAc/hexanes) gave the desired product. $^1$H NMR (500 MHz, CDCl$_3$) δ1.09–1.33 (m, 5H), 1.66–1.73 (m, 2H), 1.75–1.83 (m, 2H), 2.01–2.08 (m, 1H), 4.98 (d, 1H), 5.27 (d, 1H), 5.29 (d, 1H), 7.35–7.4 (m, 5H).

Step C: Benzyl (2R)-cyclohexyl[(3S,4R)-3-(3-fluorophenyl)-4-(hydroxymethyl)pyrrolidin-1-yl]ethanoate A solution of Pyrrolidine 2 (3.1 g, 10 mmol) in 25 mL CH$_2$Cl$_2$ was cooled in an ice bath and DIEA (2.96 mL, 17 mmol) was added. A solution of enzyl (2S)-cyclohexyl{[(trifluoromethyl)sulfonyl]oxy}ethanoate (3.8 g, 10 mmol, from Step B) in 25 mL CH$_2$Cl$_2$ was added. The mixture was warmed to rt and stirred for 24 h. The solution was diluted with 75 mL CH$_2$Cl$_2$ and washed with 1 M NaOH and sat'd NaCl. The organic portions were dried over sodium sulfate and concentrated. Flash chromatography (150 g silica, 0→10% EtOAc/hexane with 1% TEA) gave 5.3 g (99%) of product. The material was dissolved in 50 mL THF and a solution of tetrabutylammonium fluoride (18 mL, 1 M in THF, 18 mmol) was added. After 90 min the mixture was poured into 150 mL ice water and extracted with 300 mL ether. The organic portion was dried and concentrated. Flash chromatography (150 g silica, 20→40% EtOAc/hexane with 1% TEA) gave the desired product. $^1$H NMR (500 MHz, CDCl$_3$) δ0.9–1.06 (m, 2H), 1.12–1.28 (m, 3H), 1.58–1.82 (m, 5H), 1.9–1.97 (m, 1H), 2.28–2.34 (m, 1H), 2.60 (dd, 1H), 2.75 (dd, 1H), 3.07 (dd, 1H), 3.14 (dd, 1H), 3.19 (d, 1H), 3.26–3.30 (m, 1H), 3.54–3.59 (m, 1H), 3.66–3.69 (m, 1H), 5.18 (d, 1H), 5.19 (d, 1H), 6.88–6.93 (m, 2H), 6.95–6.98 (m, 1H), 7.21–7.26 (m 1H), 7.32–7.41 (m, 5H).

Step D: Benzyl (2R)-cyclohexyl[(3S,4R)-3-(3-fluorophenyl)-4-formylpyrrolidin-1-yl]ethanoate A solution of oxalyl chloride (1.03 mL, 11.8 mmol) in 60 mL CH$_2$Cl$_2$ was cooled in a dry ice/acetone bath. DMSO (1.67 mL, 23.6 mmol) was added dropwise. The mixture was stirred for 15 min then a solution of benzyl (2R)-cyclohexyl [(3S,4R)-3-(3-fluorophenyl)-4-(hydroxymethyl)pyrrolidin-1-yl]ethanoate (4.2 g, 9.8 mmol, from Step C) in 70 mL CH$_2$Cl$_2$ was added dropwise. After stirring for 15 min TEA (6.8 mL, 49 mmol) was added in 10 mL CH$_2$Cl$_2$. The mixture was warmed to rt and stirred for 2 h. The solution was poured into a speparatory funnel and diluted with 200 mL CH$_2$Cl$_2$ and washed with 1 N NaOH (2×), water and sat'd NaCl. The organic portion was dried over sodium sulfate and concentrated. Flash chromatography (150 g silica, 0→30% EtOAc/hexanes) gave the desired aldehyde. $^1$H NMR (500 MHz, CDCl$_3$) δ0.95–1.05 (m, 2H), 1.14–1.29 (m, 3H), 1.6 (br d, 1H), 1.66–1.83 (m, 4H), 1.93 (br d, 1H), 2.65–2.69 (m, 1H), 2.88–2.93 m, 1H), 3.15 (dd, 1H), 3.20–3.24 (m, 2H), 3.27–3.30 (m, 1H), 3.55 (dd, 1H), 5.18 (d, 1H), 5.19 (d, 1H), 6.89–6.97 m, 3H), 7.23–7.27 (m, 1H), 7.33–7.4 (m, 5H).

Aldehyde 2

Benzyl 1-{[(3S,4R)-3-(3-fluorophenyl)-4-formylpyrrolidin-1-yl]methyl}cyclohexanecarboxylate

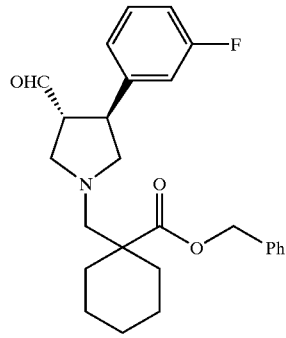

Step A: Dibenzyl cyclohexane-1,1-dicarboxylate

A solution of dibenzyl malonate (40 g, 161 mmol), 1,5-dibromopentane (22 mL, 161 mmol) and potassium carbonate (56 g, 402 mmol) in 300 mL of DMSO was stirred for 48 h in an oil bath at 50° C. The mixture was diluted with water and extracted with ethyl acetate (2×). The combined organic portions were dried over magnesium sulfate and concentrated. Flash chromatography (400 g silica, 15/1 hexane/EtOAc) gave the desired product. $^1$H NMR (500 MHz, CDCl$_3$) δ1.4–1.5 (m, 1H), 1.52–1.6 (m, 5H), 2.03–2.1 (m, 4H), 5.13 (s, 4H), 7.22–7.38 (m, 10H).

Step B: Benzyl 1-formylcyclohexanecarboxylate

A solution of dibenzyl cyclohexane-1,1-dicarboxylate (10.5 g, 30 mmol, from Step A) in 100 mL CH$_2$Cl$_2$ was cooled to −78° C. and a solution of diisobutylaluminum hydride (60 mL, 1 M in CH$_2$Cl$_2$, 60 mmol) was added dropwise. After 3.5 h the mixture was carefully quenched with sat'd ammonium chloride and 1 M HCl. The mixture was warmed to rt and poured into 200 mL water and 200 mmL CH$_2$Cl$_2$. The layers were separated and the aqueous layer was extracted with CH$_2$Cl$_2$. The combined organic layers were dried over magnesium sulfate and concentrated. Flash chromatography (400 g silica, 10/1 hexane/EtOAc) gave 5.9 g (79%) of the desired aldehyde. $^1$H NMR (500 MHz, CDCl$_3$) δ1.4–1.6 (m, 16), 1.88–1.95 (m, 2H), 2.03–2.12 (m, 2H), 5.2 (s, 2H), 7.30–7.41 (m, 5H), 9.58 (s, 1H).

Step C: Benzyl 1-{[(3R,4S)-3-(3-fluorophenyl)-4-(hydroxymethyl)pyrrolidin-1-yl]methyl}cyclohexanecarboxylate A solution of pyrrolidine 2 (6.27 g, 20.3 mmol), Benzyl 1-formyl cyclohexanecarboxylate (5 g, 20.3 mmol, from Step B), DIEA (8.8 mL, 50.7 mmol) and sodium triacetoxyborohydride (10.3 g, 50.7 mmol) in 100 mL DCE was stirred for 12 h. The solution was diluted with water and extracted with CH$_2$Cl$_2$ (2×). The combined organic phases were washed with sat'd NaCl then dried over magnesium sulfate and concentrated. Flash chromatography (450 g silica, 15/1 hexane/EtOAc) afforded 6.01 g (55%) of product. The silyl ether was dissolved in 12 mL THF and a solution of tetra-n-butyl ammonium fluoride (17 mL, 1.0 M in THF, 17 mmol) was added. After stirring for 3 h the solvent was removed and the crude mixture was purified by flash chromatography (450 g silica, 3/1 hexane/EtOAc→2/1 hexane/EtOAc) to give the desired product. $^1$H NMR (500 MHz, CDCl$_3$) δ1.24–1.36 (m, 4H), 1.37–1.46 (m, 2H), 1.55–1.62 (m, 4H), 2.11–2.25 (m, 3H), 2.44–2.49 (m, 2H), 2.67–2.72 (m, 2H), 2.80–2.84 (dd, 1H), 3.07–3.12 (dd, 2H), 3.55–3.58 (dd, 1H), 3.66–3.69 (dd, 1H), 5.14–5.22 (dd, 2H), 6.88–6.92 (m, 1H), 6.95–6.97 (m, 1H), 6.66–7.01 (m, 1H), 7.22–7.26 (m, 1H), 7.3–7.41 (m, 5H).

Step D: Benzyl 1-{[(3R,4S)-3-(3-fluorophenyl)-4-formylpyrrolidin-1-yl]methyl}cyclohexanecarboxylate A solution of oxalyl chloride (0.6 mL, 7 mmol) in 35 mL CH$_2$Cl$_2$ was cooled to −78° C. and DMSO (1 mL, 14.1 mmol) was added dropwise. After stirring for 20 min a solution of Benzyl 1-{[(3R,4S)-3-(3-fluorophenyl)-4-(hydroxymethyl)pyrrolidin-1-yl]methyl}cyclohexane carboxylate (2.5 g, 5.88 mmol, from Step C) in 35 mL CH$_2$Cl$_2$ was added. The mixture was stirred for 20 min more then triethylamine (4 mL, 29.5 mmol) was added. The cooling bath was removed and the mixture was stirred for 4h. 100 mL CH$_2$Cl$_2$ was added and the mixture was washed with 1 M NaOH then water and sat'd sodium chloride. The organic layer was dried over magnesium sulfate and concentrated. Flash chromatography (90 g silica, 5/1 hexane/EtOAc) gave the desired aldehyde. $^1$H NMR (500 MHz, CDCl$_3$) δ1.25–1.43 (m, 6H), 1.58–1.63 (m, 4H), 2.15–2.19 (m, 2H), 2.62–2.73 (m, 2H), 2.83–2.87 (m, 1H), 2.92–3.01 (m, 2H), 3.44–3.51 (m, 1H), 5.11–5.21 (dd, 2H), 6.9–6.97 (m, 1H), 6.98–7.13 (m, 2H), 7.23–7.4 (m, 6H), 9.6 (s, 1H).

Intermediate 3

Ethyl 3-exo-[(2-aminophenyl)amino]-8-azabicyclo[3.2.1]octane-8-carboxylate

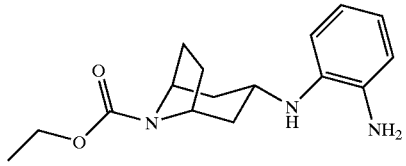

Step A: 2-exo-(8-Methyl-8-azabicyclo[3.2.1]oct-3-yl)-1H-isoindole-1,3(2H)-dione Tropine (20.3 g, 144 mmol), triphenylphosphine (56.6 g, 216 mmol) and phthalimide (31.8 g, 216 mmol) were dissolved in 600 mL dry THF. The solution was cooled to 0° C. and diisopropylazodicarboxylate (43 mL, 216 mmol) was added dropwise through an addition funnel. The resulting mixture was stirred at rt for a full 24 h. The solvent was removed and the residue was taken up in CH$_2$Cl$_2$ then extracted with 1 M HCl (5×100 mL). The combined acid layers were basified with potassium carbonate and extracted with CH$_2$Cl$_2$ (3×150 mL). The organic fractions were combined and dried over sodium sulfate then concentrated. Flash chromatography (450 g silica, 19/1 CH$_2$Cl$_2$/MeOH→5/1 CH$_2$Cl$_2$/MeOH) gave the desired product. $^1$H NMR (500 MHz, CDCl$_3$) δ1.4–1.5 (mn, 2H), 1.75 (m, 2H), 2.15 (m, 2H), 2.51 (s, 3H), 2.65 (t, 2H), 3.3–3.35 (m, 2H), 4.5–4.6 (m, 1H), 7.7–7.73 (d, 2H), 7.82–7.85 (d, 2H).

Step B: Ethyl 3-exo-(1,3-dioxo-1,3-dihydro-2H-isoindol-2-yl)-8-azabicyclo[3.2.1]octane-8-carboxylate A solution of 2-(8-methyl-8-azabicyclo[3.2.1]oct-3-yl)-1H-isoindole-1,3(2H)-dione (3.0 g, 11.1 mmol, from Step A)

and ethyl chloroformate (2.9 mL, 30 mmol) in 30 mL toluene was heated to 90° C. for 6 h. The solution was cooled and extracted with 1 M HCl. The organic layer was dried over sodium sulfate and concentrated to give the desired product. $^1$H NMR (500 MHz, CDCl$_3$) δ1.33 (t, 3H), 1.6–1.65 (m, 2H), 1.8–1.9 (m, 2H), 2.02–2.13 (m, 2H), 2.6–2.7 (m, 2H), 4.2–4.5 (m, 4H), 4.62–4.74 9m, 1H), 7.7–7.73 (d, 2H), 7.82–7.85 (d, 2H).

Step C: Ethyl 3-exo-amino-8-azabicyclo[3.2.1]octane-8-carboxylate

Ethyl 3-exo-(1,3-dioxo-1,3-dihydro-2H-isoindol-2-yl)-8-azabicyclo[3.2.1]octane-8-carboxylate (3.4 g, 10.4 mmol, from Step B) and hydrazine (0.7 mL, 22.8 mmol) were dissolved in 30 mL of ethanol and the mixture was refluxed for 4 h. The mixture was diluted with water and conc. HCl resulting in the formation of a white precipitate. The precipitate was filtered and the aqueous solution was basified with potassium carbonate then extracted with CH$_2$Cl$_2$. Drying over sodium sulfate and removal of solvent afforded the desired product. $^1$H NMR (300 MHz, CDCl$_3$) δ1.25 (t, 3H), 1.4–1.6 (m, 2H), 1.65 (m, 2H), 1.85 (m, 2H), 1.99 (m, 2H), 2.41 (br s, 2H), 3.2 (m, 1H), 4.13 (q, 2H), 4.3 (br s, 2H).

Step D: Ethyl 3-exo-[(2-aminophenyl)amino]-8-azabicyclo[3.2.1]octane-8-carboxylate A solution of ethyl 3-exo-amino-8-azabicyclo[3.2.1]octane-8-carboxylate (1.8 g, 9.1 mmol, from Step C), potassium carbonate (1.27 g, 9.2 mmol) and 2-fluoronitrobenzene (1.05 mL, 10 mmol) in 6 mL DMF was heated to 150° C. for 3 h. The mixture was cooled and the solvent was removed. The residue was diluted with EtOAc and washed with water and sat'd NaCl. The organic portion was dried and concentrated. Flash chromatography (9/1→7/3 hexane/EtOAc) gave 2.4 g (83%) of product. The product was dissolved in 43 mL EtOAc and 7.5 mL methanol and 10% palladium on carbon was added (0.4 g, 0.38 mmol). The reaction mixture was stirred under 1 atmosphere of hydrogen for 12 h. The mixture was filtered and concentrated to afford pure product. $^1$H NMR (300 MHz, CDCl$_3$) δ1.29 (t, 3H), 1.42–1.62 (m, 2H), 1.8 (m, 2H), 2.0–2.2 (m, 4H), 3.2–3.3 (br s, 2H), 3.8 (m, 1H), 4.15 (q, 2H), 4.4 (br s, 2H), 6.65–6.8 (m, 4H).

Intermediate 4 tert-Butyl 3-endo-[(2-aminophenyl)amino]-8-azabicyclo[3.2.1]octane-8-carboxylate

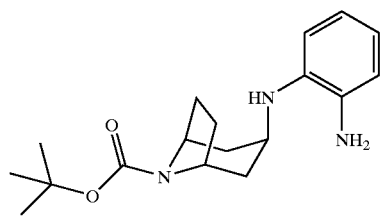

Step A: 8-Benzyl-8-azabicyclo[3.2.1]octan-3-one 2,5-dimethoxytetrahydrofuran (17.1 g, 132.2 mmol) was dissolved in 0.025 M HCl (56 mL) and the mixture was stirred at 0° C. for 16 h. Benzylamine hydrochloride (22.8 g, 158.6 mmol) and 3-oxopentanedioic acid (19.3 g, 132.2 mmol) followed by aqueous sodium acetate (105 mL, 0.69 M). The reaction mixture was warmed to room temperature and stirred for 1h then heated to 50° C. for 1.5 h. After cooling back to rt the mixture was basified with sodium hydroxide and extracted with EtOAc (3×) The combined organic portions were dried over sodium sulfate and concentrated. Flash chromatography (450 g silica, 50/1 CH$_2$Cl$_2$/MeOH), gave the desired product. $^1$H NMR (500 MHz, CDCl$_3$) δ1.65 (m, 2H), 2.05–2.15 (m, 2H), 2.2 (s, 1H), 2.23 (s, 1H), 2.69 (m, 1H), 2.72 (m, 1H), 3.48 (s, 2H), 7.2–7.3 (m, 1H), 7.33–7.4 (m, 4H).

Step B: tert-Butyl 3-oxo-8-azabicyclo[3.2.1]octane-8-carboxylate

A solution of 8-benzyl-8-azabicyclo[3.2.1]octan-3-one (5.1 g, 23.7 mmol), di-tert-butyldicarbonate (6.2 g, 28.5 mmol, from Step A) and palladium hydroxide (1.1 g, 20% wt. on carbon, 1.2 mmol) in 56 mL EtOAc was shaken in a Parr® shaker under 40 psig of hydrogen. After 9 h the catalyst was filtered off and the solvent was removed. Flash chromatography (90 g silica, 9/1 hexane/EtOAc) gave the desired product.

Step C: tert-Butyl 3-endo-amino-8-azabicyclo[3.2.1]octane-8-carboxylate

A solution of sodium triacetoxyborohydride (5.5 g, 25.8 mmol), benzyl amine (2.1 mmL, 19 mmol) and tert-Butyl 3-oxo-8-azabicyclo[3.2.1]octane-8-carboxylate (3.88 g, 17.2 mmol, from Step B) in 113 mL dichloroethane was stirred for 48 h. The mixture was diluted with EtOAc and washed with sat'd sodium carbonate. The organic phase was dried over sodium sulfate and concentrated. Flash chromatography (90 g silica, 99/1/0.1 CH$_2$Cl$_2$/MeOH/NH$_3$) gave 4.17 g (77%) product. The product was dissolved in 120 mL ethanol and palladium hydroxide (0.59 g, 0.66 mmol) then ammonium formate (4.2 g, 66 mmol) were added. The mixture was heated to 50° C. until no further gas evolution occurred. The mixture was cooled, filtered and concentrated. Flash chromatography (90 g silica, 2% 2 M ammonia/methanol in CH$_2$Cl$_2$→5% 2 M ammonia/methanol in CH$_2$Cl$_2$) gave the desired product.

Step D: tert-Butyl 3-[(2-aminophenyl)amino]-8-azabicyclo[3.2.1]octane-8-carboxylate The title compound was prepared according to the procedure described for Intermediate 3 Step D. Starting with 1.65 g of tert-butyl 3-endo-amino-8-azabicyclo[3.2.1]octane-8-carboxylate, the desired final product was obtained. ESI-MS (M+H) calc. 334.24, found. 334.3

Amine 1

1-exo-(8-Azabicyclo[3.2.1]oct-3-yl)-2-ethyl-1H-benzimidazole

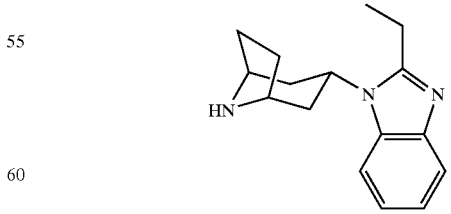

A solution of ethyl 3-exo-[(2-aminophenyl)amino]-8-azabicyclo[3.2.1]octane-8-carboxylate (0.4 g, 1.4 mmol, Intermediate 3) in 8 mL of trimethyl-ortho-propionate was refluxed for 18 h. The mixture was concentrated and the residue was dissolved in 6 M HCl and refluxed for 28 h. After cooling the mixture was neutralized with sodium hydroxide and extracted with $CH_2Cl_2$ (4×). The combined organic portions were dried over sodium sulfate and concentrated. Flash chromatography (40 g silica, 95/5 $CH_2Cl_2$/MeOH→90/10/1 $CH_2Cl_2$/MeOH/$NH_3$) gave 256 mg product. ESI-MS (M+H) calc. 256.2, found. 256.3.

Amine 2

1-exo-(8-Azabicyclo[3.2.1]oct-3-yl)-2-methyl-1H-benzimidazole

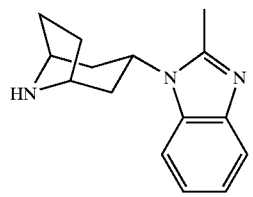

The title compound was prepared according to the procedure described for amine 1 using trimethyl-ortho-acetate and 3-exo-[(2-aminophenyl)amino]-8-azabicyclo[3.2.1]octane-8-carboxylate (0.8 g, 1.4 mmol, Intermediate 3). ESI-MS (M+H) calc. 242.2, found. 242.3.

Amine 3

1-exo-(8-azabicyclo[3.2.1]oct-3-yl)-1H-benzimidazole

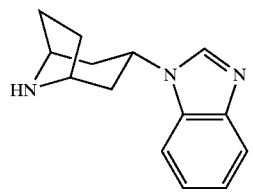

The title compound was prepared according to the procedure described for amine 1 using trimethyl-ortho-formate and 3-exo-[(2-aminophenyl)amino]-8-azabicyclo[3.2.1]octane-8-carboxylate (0.8 g, 1.4 mmol, Intermediate 3). ESI-MS (M+H) calc. 228.1, found. 228.2.

Amine 4

1-endo-(8-Azabicyclo[3.2.1]oct-3-yl)-2-ethyl-1H-benzimidazole

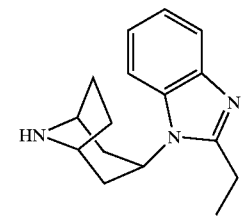

The title compound was prepared according to the procedure described for amine 1 using trimethyl-ortho-propionate and 3-endo-[(2-aminophenyl)amino]-8-azabicyclo[3.2.1]octane-8-carboxylate (Intermediate 4). ESI-MS (M+H) calc. 256.2, found. 256.3.

Amine 5

1-endo-(8-Azabicyclo[3.2.]oct-3-yl)-2-methyl-1H-benzimidazole

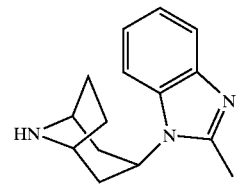

The title compound was prepared according to the procedure described for amine 1 using trimethyl-ortho-acetate and 3-endo-[(2-aminophenyl)amino]-8-azabicyclo[3.2.1]octane-8-carboxylate (Intermediate 4). ESI-MS (M+H) calc. 242.2, found. 242.3.

Amine 6

1-endo-(8-azabicyclo[3.2.1]oct-3-yl)-1H-benzimidazole

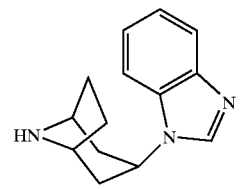

The title compound was prepared according to the procedure described for amine 1 using trimethyl-ortho-formate and 3-endo-[(2-aminophenyl)amino]-8azabicyclo[3.2.1]octane-8-carboxylate (Intermediate 4). ESI-MS (M+H) calc. 228.1, found. 228.2.

EXAMPLES

General Procedure

A solution of the appropriate amine (1.0 equiv) and the appropriate aldehyde (1.0 equiv) in dichloroethane was stirred with sodium triacetoxyborohydride (2.0 equiv). After complete reaction the mixture was filtered through a plug of silica gel eluting with 20/1 $CH_2Cl_2$/MeOH. The crude product was hydrogenated (10 mol % Pd/C, 1 atm hydrogen, MeOH) then purified by semi-prep HPLC (YMC combi-prep column, 5%→90% acetonitrile/water with 0.1% TFA, flow=10 mL/min).

Example 1

(2R)-[(3R,4S)-3-{[3-exo-(1H-Benzimidazol-1-yl)-8-azabicyclo[3.2.1]oct-8-yl]methyl}-4-(3-fluorophenyl)pyrrolidin-1-yl](cyclohexyl)ethanoic acid

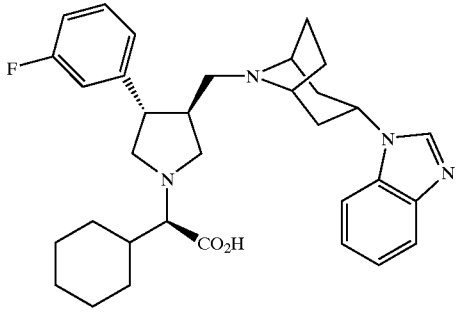

The title compound was prepared from amine 3 (14 mg, 0.06 mmol) and aldehyde 1 (25 mg, 0.06 mmol) according to the general procedure. The product was obtained a white solid. $^1$H NMR (500 MHz, CD$_3$OD) δ1.1–2.4 (14H), 2.8–3.1 (4H), 3.3–4.1 (13H) 7.08–7.18 (m, 1H), 7.28–7.35 (m, 2H), 7.42–7.6 (m, 5H), 7.73–7.76 (d, 1H), 8.1–8.2 (m, 1H). ESI-MS (M+H) calc. 545.32, found. 545.4.

Example 2

(2R)-Cyclohexyl((3S,4R)-3-(3-fluorophenyl)-4-{[3-exo-(2-methyl-1H-benzimidazol-1-yl)-8-azabicyclo[3.2.1]oct-8-yl]methyl}pyrrolidin-1-yl)ethanoic acid

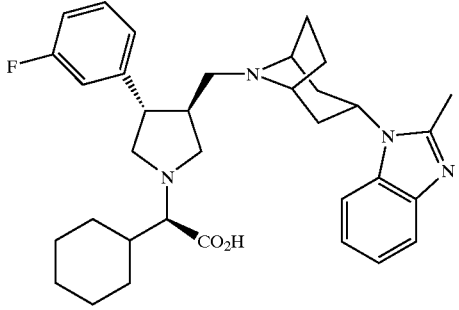

The title compound was prepared according to the general procedure from aldehyde 1 (25 mg, 0.06 mmol) and amine 2 (15 mg, 0.06 mmol). ESI-MS (M+H) calc. 559.34, found. 559.4.

Example 3

(2R)-Cyclohexyl[(3R,4S)-3-{[3-exo-(2-ethyl-1H-benzimidazol-1-yl)-8-azabicyclo[3.2.1]oct-8-yl]methyl}-4-(3-fluorophenyl)pyrrolidin-1-yl]ethanoic acid

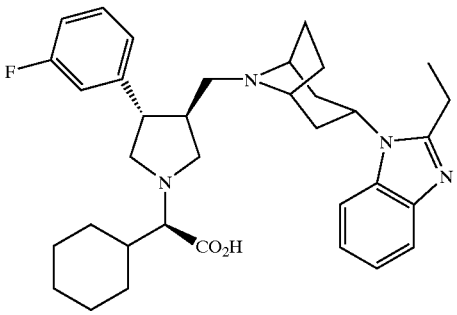

The title compound was prepared according to the general procedure from aldehyde 1 (25 mg, 0.06 mmol) and amine 1 (16 mg, 0.06 mmol). ESI-MS (M+H) calc. 573.35, found. 573.4.

Example 4

(2R)-[(3R,4S)-3-{[3-endo-(1H-Benzimidazol-1-yl)-8-azabicyclo[3.2.1]oct-8-yl]methyl}-4-(3-fluorophenyl)pyrrolidin-1-yl](cyclohexyl)ethanoic acid

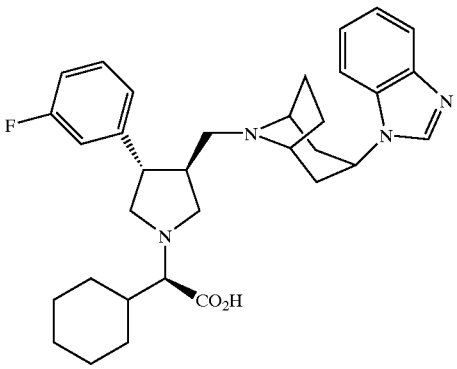

The title compound was prepared according to the general procedure from aldehyde 1 (25 mg, 0.06 mmol) and amine 6 (14 mg, 0.06 mmol). $^1$H NMR (500 MHz, CD$_3$OD) δ1.1–1.4 (m, 4H), 1.42–2.3 (14H), 2.3–2.4 (m, 1H), 2.43–2.53 (m, 2H), 2.55–2.7 (m, 11H), 2.8–2.9 (m, 11H), 3.3–3.4 (m, 21H), 3.42–3.78 (5H), 4.44–4.51 (m, 1H), 7.0–7.05 (m, 1H), 7.23–7.48 (m, 6H), 7.65–7.68 (d, 1H), 8.25 (s, 1H), ESI-MS (M+H) calc. 545.32, found. 545.4.

Example 5

(2R)-Cyclohexyl((3S,4R)-3-(3-fluorophenyl)-4-{[3-endo-(2-methyl-1H-benzimidazol-1-yl)-8-azabicyclo[3.2.1]oct-8-yl]methyl}pyrrolidin-1-yl)ethanoic acid

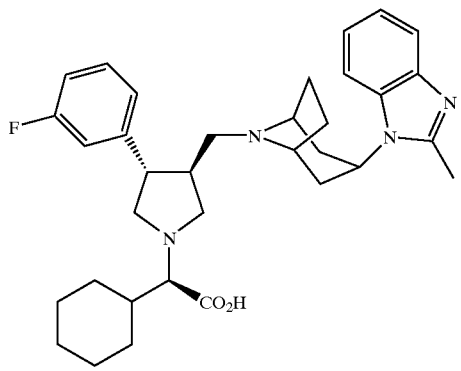

The title compound was prepared according to the general procedure from aldehyde 1 (25 mg, 0.06 mmol) and amine 5 (15 mg, 0.06 mmol). ESI-MS (M+H) calc. 559.34, found. 559.4.

Example 6

(2R)-Cyclohexyl[(3R,4S)-3-{[3-endo-(2-ethyl-1H-benzimidazol-1-yl)-8-azabicyclo[3.2.1]oct-8-yl]methyl}-4-(3-fluorophenyl)pyrrolidin-1-yl]ethanoic acid

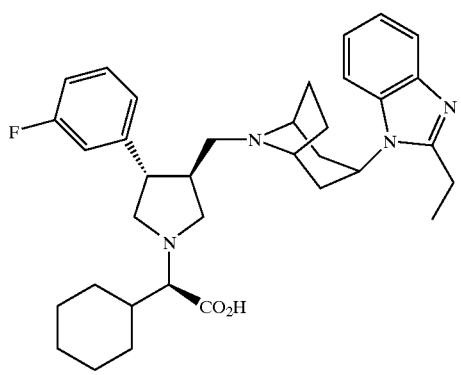

The title compound was prepared according to the general procedure from aldehyde 1 (25 mg, 0.06 mmol) and amine 4 (15 mg, 0.06 mmol). ESI-MS (M+H) calc. 573.35, found. 573.4.

Example 7

1-{[(3R,4S)-3-{[3-exo-(1H-Benzimidazol-1-yl)-8-azabicyclo[3.2.1]oct-8-yl]methyl}-4-(3-fluorophenyl)pyrrolidin-1-yl]methyl}cyclohexanecarboxylic acid

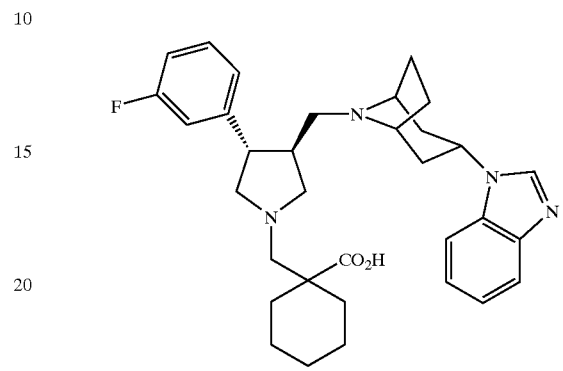

The title compound was prepared according to the general procedure from aldehyde 2 (30 mg, 0.07 mmol) and amine 3 (16 mg, 0.07 mmol). ESI-MS (M+H) calc. 545.32, found. 545.4.

Example 8

1-[((3S,4R)-3-(3-Fluorophenyl)-4-{[3-exo-(2-methyl-1H-benzimidazol-1-yl)-8-azabicyclo[3.2.1]oct-8-yl]methyl}pyrrolidin-1-yl)methyl]cyclohexanecarboxylic acid

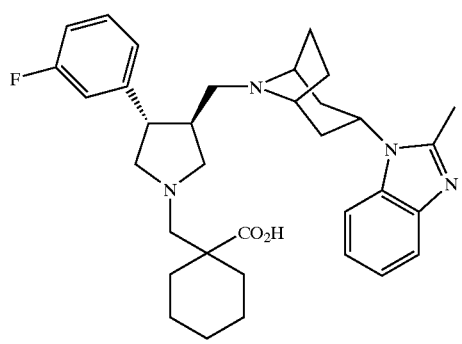

The title compound was prepared according to the general procedure from aldehyde 2 (30 mg, 0.07 mmol) and amine 2 (17 mg, 0.07 mmol). ESI-MS (M+H) calc. 559.34, found. 559.4.

Example 9

1-{[(3R,4S)-3-{[3-exo-(2-Ethyl-1H-benzimidazol-1-yl)-8-azabicyclo[3.2.1]oct-8-yl]methyl}-4-(3-fluorophenyl)pyrrolidin-1-yl]methyl}cyclohexanecarboxylic acid

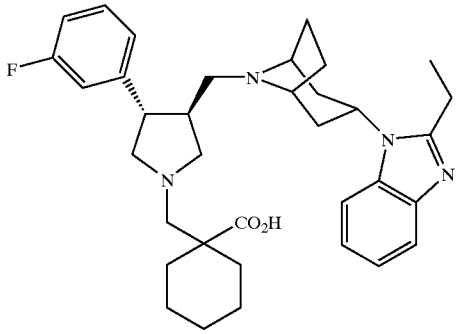

The title compound was prepared according to the general procedure from aldehyde 2 (30 mg, 0.07 mmol) and amine 1 (18 mg, 0.07 mmol). ESI-MS (M+H) calc. 573.35, found. 573.4.

Example 10

1-{[(3R,4S)-3-{[3-endo-(1H-Benzimidazol-1-yl)-8-azabicyclo[3.2.1]oct-8-yl]methyl}-4-(3-fluorophenyl)pyrrolidin-1-yl]methyl}cyclohexanecarboxylic acid

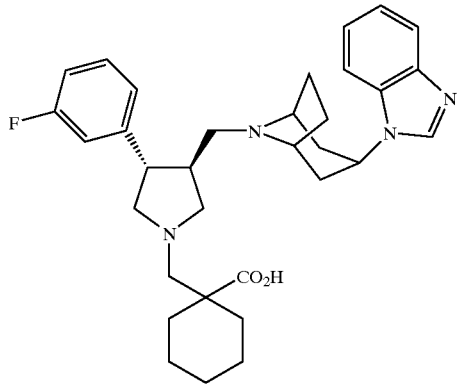

The title compound was prepared according to the general procedure from aldehyde 2 (25 mg, 0.06 mmol) and amine 6 (14 mg, 0.06 mmol). ESI-MS (M+H) calc. 545.32, found. 545.4.

Example 11

1-[((3S,4R)-3-(3-Fluorophenyl)-4-{[3-endo-(2-methyl-1H-benzimidazol-1-yl)-8-azabicyclo[3.2.1]oct-8-yl]methyl}pyrrolidin-1-yl)methyl]cyclohexanecarboxylic acid

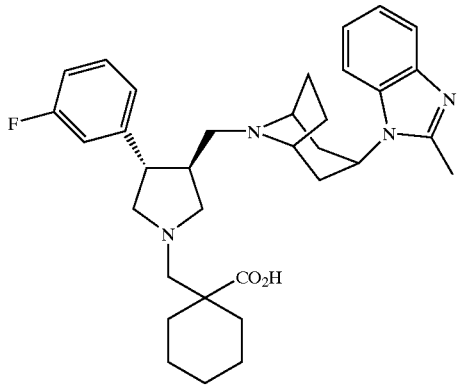

The title compound was prepared according to the general procedure from aldehyde 2 (25 mg, 0.06 mmol) and amine 5 (16 mg, 0.06 mmol). ESI-MS (M+H) calc. 559.34, found. 559.4.

Example 12

1-{[(3R,4S)-3-{[3-endo-(2-Ethyl-1H-benzimidazol-1-yl)-8-azabicyclo[3.2.1]oct-8-yl]methyl}-4-(3-fluorophenyl)pyrrolidin-1-yl]methyl}cyclohexanecarboxylic acid

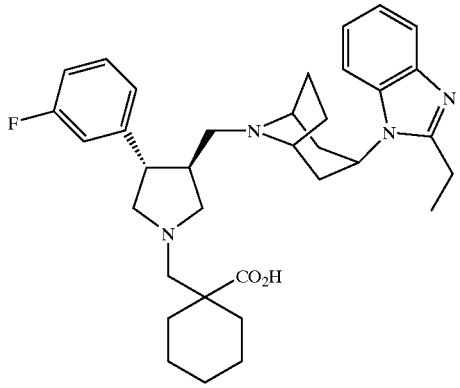

The title compound was prepared according to the general procedure from aldehyde 2 (25 mg, 0.06 mmol) and amine 4 (16 mg, 0.06 mmol). ESI-MS (M+H) calc. 573.35, found. 573.4.

Examples 13–16

Examples 13–16 in the Table below were prepared from the corresponding bicyclic piperidine and aldehyde using procedure similar to those described for other examples. The aldehyde used was Aldehyde 1. The benzyl ester was removed first by hydrogenation with Pd/C followed by reductive amination with the bicyclic piperidines. The 7-(exo-2-Methyl-1H-benzimidazol-1-yl)-3-thia-9-azabicyclo[3.3.1]nonane and 7-(exo-2-Methyl-1H-benzimidazol-1-yl)-3-oxa-9-azabicyclo[3.3.1]nonane were prepared using procedures described in WO 00/38680, 2000 by Duncan, et al. The other two piperidines were prepared similarly using appropriate orthoformates. All of the compounds were prepared as the tris-TFA salts.

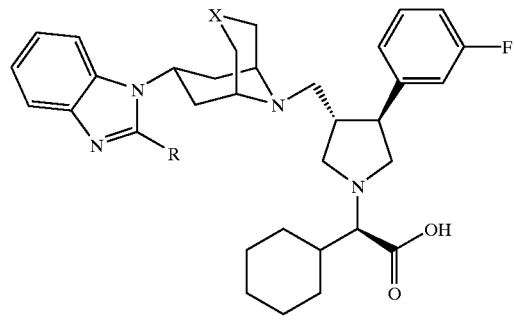

| EXAMPLE # | R | X | ESI-MS (M + H) | HPLC |
|---|---|---|---|---|
| 13 | Methyl | O | 575.3 m/Z | 3.10 min. |
| 14 | Methyl | S | 591.3 m/Z | 3.41 min. |
| 15 | H | S | 577.3 m/Z | 3.41 min. |
| 16 | Ethyl | S | 605.3 m/Z | 3.50 min. |

Examples 17–20

Examples 17–20 in the Table below were prepared from the corresponding bicyclic piperidine and aldehyde using the same procedure as the above four examples except Aldehyde 2 was used here. All of the compounds were prepared as tris-TFA salts.

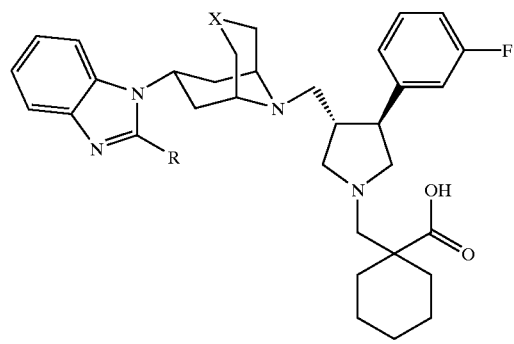

| EXAMPLE # | R | X | ESI-MS (M + H) | HPLC |
|---|---|---|---|---|
| 17 | Methyl | O | 575.3 m/Z | 3.05 min. |
| 18 | Methyl | S | 591.4 m/Z | 3.29 min. |
| 19 | H | S | 577.3 m/Z | 3.33 min. |
| 20 | Ethyl | S | 605.4 m/Z | 3.44 min. |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

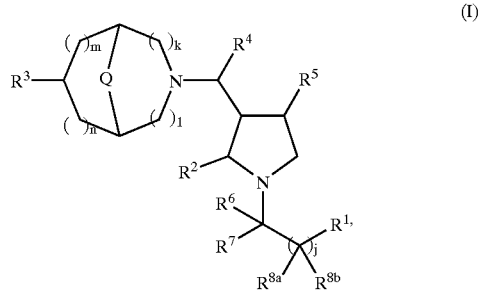

(I)

wherein:
R$^1$ is selected from:
(1) —CO$_2$H,
(2) —NO$_2$,
(3) -tetrazolyl,
(4) -hydroxyisoxazole,
(5) —SO$_2$NHCO—(C$_{0-3}$ alkyl)-R$^9$, wherein R$^9$ is independently selected from hydrogen, C$_{1-6}$ alkyl, C$_{5-6}$ cycloalkyl, benzyl or phenyl, wherein alkyl, cycloalkyl, benzyl or phenyl is unsubstituted or substituted with 1–3 substituents independently selected from halo, C$_{1-3}$ alkyl, —O—C$_{1-3}$ alkyl and trifluoromethyl, and
(6) —P(O)(OH)$_2$;

j is an integer which is 0, 1, 2 or 3;
R$^2$ is hydrogen or C$_{1-6}$ alkyl;
Q is —(CH$_2$)$_{1-3}$—, —CH$_2$OCH$_2$—, —CH$_2$SCH$_2$—, —CH$_2$S(O)CH$_2$—, —CH$_2$S(O$_2$)CH$_2$—, or —CH$_2$N(R$^d$)CH$_2$—;
k, l, m and n are each independently integers from zero to 3;
R$^3$ is phenyl, naphthyl, or heterocycle, wherein any one of which is optionally substituted with from 1 to 7 of R$^{11}$ where R$^{11}$ is independently selected from:
(a) halo,
(b) cyano,
(c) hydroxy,
(d) C$_{1-6}$ alkyl, which is unsubstituted or substituted with 1–5 of R$^{12}$ where R$^{12}$ is independently selected from halo, cyano, hydroxy, —O—C$_{1-6}$ alkyl, —C$_{3-6}$ cycloalkyl, —CO$_2$H, —CO$_2$—(C$_{1-6}$ alkyl), —CF$_3$, —SO$_2$R$^9$, —NR$^9$R$^{10}$ (where R$^9$ is independently as defined above and R$^{10}$ is independently selected from the definitions of R$^9$), phenyl, naphthyl, biphenyl, and heterocycle;
wherein phenyl, naphthyl, biphenyl, or heterocycle is unsubstituted or substituted with 1–7 of R$^{13}$ where R$^{13}$ is independently selected from halo, cyano, hydroxy, C$_{1-6}$ alkyl, C$_{1-6}$ haloalkyl, —O—C$_{1-6}$ alkyl, —O—C$_{1-6}$ haloalkyl, —CO$_2$H, —CO$_2$(C$_{1-6}$ alkyl), —NR$^9$R$^{10}$, —(C$_{1-6}$ alkyl)-NR$^9$R$^{10}$, —SO$_2$R$^9$, —(C$_{1-6}$ alkyl)hydroxy, —O—C$_{3-6}$ cycloalkyl, benzyloxy, phenoxy, and —NO$_2$, (e) —O—$C_{1-6}$ alkyl, which is unsubstituted or substituted with 1–5 of $R^{12}$,
(f) —O-phenyl, which is unsubstituted or substituted with 1–5 of $R^{13}$,
(g) —O-heterocycle, which is unsubstituted or substituted with 1–5 of $R^{13}$,
(h) —$NO_2$,
(i) phenyl,
(j) —$CO_2R^9$,
(k) tetrazolyl,
(l) —$NR^9R^{10}$,
(m) —$NR^9$—$COR^{10}$,
(n) —$NR^9$—$CO_2R^{10}$,
(o) —CO—$NR^9R^{10}$,
(p) —OCO—$NR^9R^{10}$,
(q) —$NR^9CO$—$NR^9R^{10}$,
(r) —$S(O)_m$—$R^9$, wherein m is an integer selected from 0, 1 and 2,
(s) —$S(O)_2$—$NR^9R^{10}$,
(t) —$NR^9S(O)_2$—$R^{10}$,
(u) —$NR^9S(O)_2$—$NR^9R^{10}$,
(v) —$C_{2-6}$ alkenyl,
(w) furanyl, which is unsubstituted or substituted with benzyl which is unsubstituted or substituted with 1–7 of $R^{13}$ wherein $R^{13}$ is independently as defined above,
(x) —$C_{3-6}$ cycloalkyl,
(y) —O—$C_{3-6}$ cycloalkyl, and
(y) oxo;

$R^4$ is hydrogen or $C_{1-6}$ alkyl;

$R^5$ is phenyl, naphthyl, or heterocycle, wherein any one of which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^6$ is hydrogen, $C_{1-10}$ alkyl, $C_{3-8}$ cycloalkyl, —($C_{1-3}$ alkyl)-$C_{3-8}$ cycloalkyl, —($C_{0-2}$ alkyl)-($C_{3-8}$ cycloalkylidenyl)-($C_{1-2}$ alkyl), $C_{2-10}$ alkenyl, $C_{2-10}$ alkynyl, cyclohexenyl, phenyl, —($C_{1-6}$ alkyl)-phenyl, naphthyl, dihydronaphthyl, tetrahydronaphthyl, octahydronaphthyl, biphenyl, or heterocycle; wherein any of which except for hydrogen is unsubstituted or substituted with 1–7 of $R^{11}$ where $R^{11}$ is independently as defined above;

$R^7$ is hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

or alternatively $R^6$ and $R^7$ together with the carbon atom to which they are attached form a $C_{3-8}$ cycloalkyl ring which may be unsubstituted or substituted with 1–7 of $R^{11}$;

$R^{8a}$ and $R^{8b}$ are each independently hydrogen, $C_{1-6}$ alkyl, $C_{2-6}$ alkenyl, $C_{2-6}$ alkynyl, $C_{3-8}$ cycloalkyl, phenyl, naphthyl, or heterocycle; wherein any one of which except hydrogen is unsubstituted or substituted with 1–7 substituents where the substituents are independently selected from:
(a) halo,
(b) $C_{1-4}$ haloalkyl,
(c) hydroxy,
(d) $C_{1-4}$ alkyl,
(e) —O—$C_{1-4}$ alkyl,
(f) —O—$C_{1-4}$ haloalkyl,
(g) $C_{3-8}$ cycloalkyl,
(h) —$CO_2R^a$,
(i) —$NR^aR^b$, and
(j) —$CONR^aR^b$;

alternatively $R^{8a}$ and $R^{8b}$ together with the carbon atom to which they are attached form:
(a) a 3- to 8-membered saturated carbocyclic ring,
(b) a 4- to 8-membered monocyclic heterocycle containing from 1 to 3 heteroatoms selected from nitrogen, oxygen and sulfur,
(c) a 5- to 8-membered saturated carbocyclic ring to which is fused a $C_{3-8}$ cycloalkyl, or
(d) a 5- to 8-membered heterocyclic ring containing from 1 to 3 heteroatoms selected from nitrogen, oxygen and sulfur, to which is fused a $C_{3-8}$ cycloalkyl, wherein the ring system of (a), (b), (c) or (d) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, and hydroxy;

or a pharmaceutically acceptable salt thereof.

2. The compound according to claim 1, wherein $R^1$ is selected from —$CO_2H$ and -tetrazolyl; or a pharmaceutically acceptable salt thereof.

3. The compound according to claim 1, wherein $R^1$ is —$CO_2H$; or a pharmaceutically acceptable salt thereof.

4. The compound according to claim 1, wherein $R^2$ is hydrogen; or a pharmaceutically acceptable salt thereof.

5. The compound according to claim 1, wherein $R^3$ is
(i) phenyl,
(ii) a 5-membered monocyclic heterocycle containing two nitrogen atoms, which is optionally substituted on one of its ring carbons with oxo and which is option ally fused with a benzene ring, or
(iii) a 5-membered monocyclic heterocycle containing two nitrogen atoms, which is optionally fused with a 5- or 6-membered heterocycle containing 1 or 2 nitrogen atoms and which is optionally substituted on any one of its ring carbons with oxo;

wherein any one of phenyl (i), heterocycle (ii), or heterocycle (iii) is optionally substituted with 1–7 substituents independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from halo, cyano, hydroxy, —O—$C_{1-6}$ alkyl, —$C_{3-5}$ cycloalkyl, —$CO_2H$, —$CO_2(C_{1-6}$ alkyl), —$CF_3$, —$SO_2R^9$, —$NR^9R^{10}$, where $R^9$ and $R^{10}$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl, phenyl, naphthyl, biphenyl, and heterocycle, which is unsubstituted or substituted with 1–7 of $R^{13}$ where $R^{13}$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^9$ and —$NR^9R^{10}$, (e) —O—$C_{1-6}$ alkyl, which is unsubstituted or substituted with 1–5 of $R^{12}$,
(f) —$NO_2$,
(g) phenyl,
(h) —$CO_2R^9$,
(i) tetrazolyl,
(j) —$NR^9R^{10}$,
(k) —$NR^9$—$COR^{10}$,
(l) —$NR^9$—$CO_2R^{10}$,
(m) —CO—$NR^9R^{10}$,
(n) —OCO—$NR^9R^{10}$,
(o) —$NR^9$CO—$NR^9R^{10}$,
(p) —$S(O)_p$—$R^9$, wherein p is an integer selected from 0, 1 and 2,
(q) —$S(O)_2$—$NR^9R^{10}$,
(r) —$NR^9S(O)_2$—$R^{10}$,
(s) —$NR^9S(O)_2$—$NR^9R^{10}$;
(t) —$C_{3-6}$ cycloalkyl, and
(u) —O—$C_{3-6}$ cycloalkyl;

or a pharmaceutically acceptable salt thereof.

6. The compound according to claim 1, wherein $R^3$ is a heterocycle selected from the group consisting of:

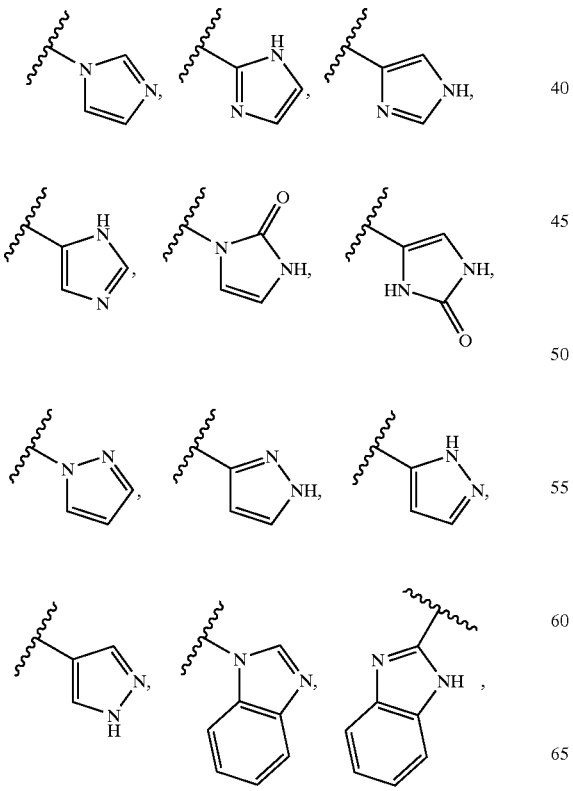

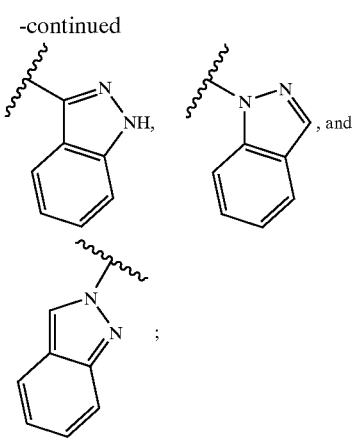

wherein "⁓"
denotes the point of attachment and wherein the heterocycle is optionally substituted with from 1 to 5 substituents independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from halo, cyano, hydroxy, —O—$C_{1-6}$ alkyl, —$C_{3-5}$ cycloalkyl, —$CO_2H$, —$CO_2(C_{1-6}$ alkyl), —$CF_3$, —$SO_2R^9$, —$NR^9R^{10}$,
where $R^9$ and $R^{10}$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl, phenyl, naphthyl, biphenyl, and heterocycle, which is unsubstituted or substituted with 1–7 of $R^{13}$ where $R^{13}$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^9$ and —$NR^9R^{10}$, (e) —O—$C_{1-6}$ alkyl, which is unsubstituted or substituted with 1–5 of $R^{12}$,
(f) —$NO_2$,
(g) phenyl,
(h) —$CO_2R^9$,
(i) tetrazolyl,
(j) —$NR^9R^{10}$,
(k) —$NR^9$—$COR^{10}$,
(l) —$NR^9$—$CO_2R^{10}$,
(m) —CO—$NR^9R^{10}$,
(n) —OCO—$NR^9R^{10}$,
(o) —$NR^9$CO—$NR^9R^{10}$,
(p) —$S(O)_p$—$R^9$, wherein p is an integer selected from 0, 1 and 2,
(q) —$S(O)_2$—$NR^9R^{10}$,
(r) —$NR^9S(O)_2$—$R^{10}$,
(s) —$NR^9S(O)_2$—$NR^9R^{10}$;
(t) —$C_{3-6}$ cycloalkyl, and
(u) —O—$C_{3-6}$ cycloalkyl;

or a pharmaceutically acceptable salt thereof.

7. The compound according to claim 1, wherein $R^3$ is

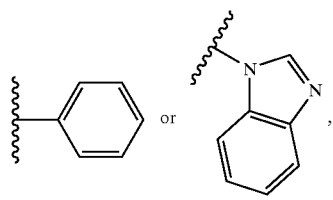

which is optionally substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—($C_{1-2}$ alkyl)
(j) phenyl,
(k) $C_{1-6}$ alkyl, which is unsubstituted or substituted with phenyl, which is unsubstituted or substituted with 1–4 of $R^f$ where $R^f$ is independently selected from halo, cyano, hydroxy, —O—$C_{1-6}$ alkyl, —O—$C_{3-5}$ cycloalkyl, —$CO_2H$, —$CO_2$($C_{1-6}$ alkyl), —$CF_3$, —$OCF_3$, and —$SO_2$—($C_{1-3}$ alkyl),
(l) —O—$C_{1-6}$ alkyl,
(m) —$C_{3-5}$ cycloalkyl,
(n) —$CH_2$—($C_{3-5}$ cycloalkyl), and
(o) —O—$C_{1-6}$ alkyl;
or a pharmaceutically acceptable salt thereof.

8. The compound according to claim 1, wherein $R^4$ is hydrogen; or a pharmaceutically acceptable salt thereof.

9. The compound according to claim 1, wherein $R^4$ is methyl; or a pharmaceutically acceptable salt thereof.

10. The compound according to claim 1, wherein $R^5$ is phenyl, thienyl, pyrazolyl, thiazolyl, thiadiazolyl, furanyl, oxadiazolyl, pyrazinyl, pyrimidinyl, or pyridyl, any one of which is unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl;
or a pharmaceutically acceptable salt thereof.

11. The compound according to claim 1 wherein $R^5$ is phenyl or thienyl, either of which is unsubstituted or substituted with 1–5 substituents where the substituents are independently selected from:
(a) halo,
(b) —$CF_3$,
(c) hydroxy, and
(d) $C_{1-3}$ alkyl;
or a pharmaceutically acceptable salt thereof.

12. The compound according to claim 1 wherein $R^5$ is phenyl, which is optionally substituted with from 1 to 5 substituents independently selected from fluoro and chloro, or unsubstituted thienyl;
or a pharmaceutically acceptable salt thereof.

13. The compound according to claim 1 wherein $R^5$ is phenyl, 3-fluorophenyl, or 3-thienyl;
or a pharmaceutically acceptable salt thereof.

14. The compound according to claim 1, wherein
Q is —$CH_2$—, —$(CH_2)_2$—, —$CH_2OCH_2$—, or —$CH_2SCH_2$—;
k and l are each independently integers from zero to 1; and
m and n are each independently integers equal to 1 or 2;
or a pharmaceutically acceptable salt thereof.

15. The compound according to claim 1, wherein
Q is —$(CH_2)_2$—, —$CH_2OCH_2$—, or —$CH_2SCH_2$—;
k and l are each integers equal to zero; and
m and n are each integers equal to 1;
or a pharmaceutically acceptable salt thereof.

16. The compound according to claim 1 wherein $R^6$ is $C_{1-10}$ alkyl, $C_{3-8}$ cycloalkyl, or —($C_{1-3}$ alkyl)-$C_{3-8}$ cycloalkyl, any one of which is unsubstituted or substituted with 1–5 substituents where the substituents are independently selected from:
(a) halo,
(b) hydroxy,
(c) —$C_{1-6}$ alkyl, which is unsubstituted or substituted with cyano, —$CO_2H$, hydroxy or trifluoromethyl,
(d) —O—$C_{1-6}$ alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$;
or a pharmaceutically acceptable salt thereof.

17. The compound according to claim 1, wherein $R^7$ is hydrogen; or a pharmaceutically acceptable salt thereof.

18. The compound according to claim 17, wherein j is an integer equal to zero; or a pharmaceutically acceptable salt thereof.

19. The compound according to claim 1, wherein $R^6$ and $R^7$ are both hydrogen; or a pharmaceutically acceptable salt thereof.

20. The compound according to claim 1, wherein $R^{8a}$ and $R^{8b}$ are each independently hydrogen, $C_{1-6}$ alkyl or $C_{3-6}$ cycloalkyl, wherein the alkyl or cycloalkyl is unsubstituted or substituted with 1–7 substituents independently selected from:
(a) halo,
(b) —$CF_3$,
(c) hydroxy, and
(d) —O—$C_{1-3}$ alkyl;
or $R^{8a}$ and $R^{8b}$ together with the carbon atom to which they are attached form:
(a) a 3- to 6-membered saturated carbocyclic ring,
(b) a 4- to 6-membered saturated heterocyclic ring containing one oxygen atom, or
(c) a 5- or 6-membered saturated carbocyclic ring to which is fused a $C_{3-6}$ cycloalkyl;
wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy;
or a pharmaceutically acceptable salt thereof.

21. The compound according to claim 1, wherein j is an integer equal to 1; or a pharmaceutically acceptable salt thereof.

22. The compound according to claim 1, wherein:
$R^6$ and $R^7$ are both hydrogen;
$R^{8a}$ and $R^{8b}$ are each independently hydrogen, $C_{1-6}$ alkyl or $C_{3-6}$ cycloalkyl, wherein the alkyl or cycloalkyl is unsubstituted or substituted with 1–7 substituents independently selected from:
(a) halo,
(b) —$CF_3$,
(c) hydroxy, and
(d) —O—$C_{1-3}$ alkyl;
or $R^{8a}$ and $R^{8b}$ together with the carbon atom to which they are attached form:
(a) a 3- to 6-membered saturated carbocyclic ring,
(b) a 4- to 6-membered saturated heterocyclic ring containing one oxygen atom, or
(c) a 5- or 6-membered saturated carbocyclic ring to which is fused a $C_{3-6}$ cycloalkyl;
wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy; and
j is an integer equal to 1;
or a pharmaceutically acceptable salt thereof.

23. The compound according to claim 1 which is of the stereochemical configuration:

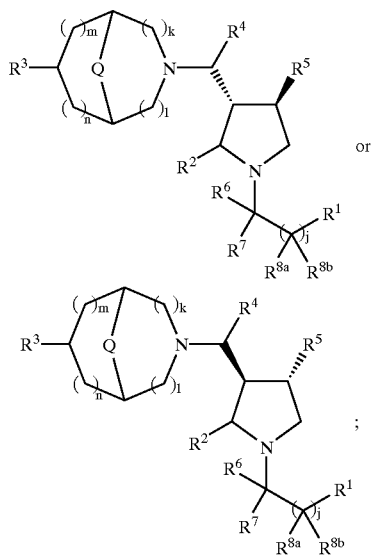

or a pharmaceutically acceptable salt thereof.

24. The compound according to claim 1, which is a compound of formula (II):

(II)

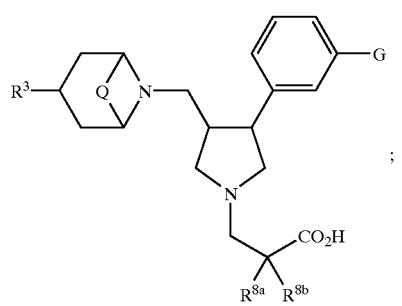

wherein
G is hydrogen or fluoro;
Q is —$(CH_2)_2$—, —$CH_2OCH_2$—, or —$CH_2SCH_2$—;

$R^3$ is:

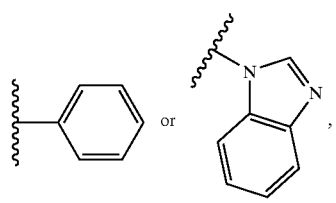

which is optionally substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) phenyl,
(h) $C_{1-6}$ alkyl, which is unsubstituted or substituted with phenyl, which is unsubstituted or substituted with 1–4 of $R^{13}$ where $R^{13}$ is independently selected from halo, cyano, hydroxy, —O—$C_{1-6}$ alkyl, —$CO_2H$, —$CO_2(C_{1-6}$ alkyl), and trifluoromethyl, and
(i) —O—$C_{1-6}$ alkyl;
$R^{8a}$ and $R^{8b}$ are each hydrogen, $C_{1-3}$ alkyl, or $C_{3-6}$ cycloalkyl;
or each of $R^{8a}$ and $R^{8b}$ is independently $C_{1-3}$ alkyl;
or $R^{8a}$ and $R^{8b}$ together with the carbon atom to which they are attached form:

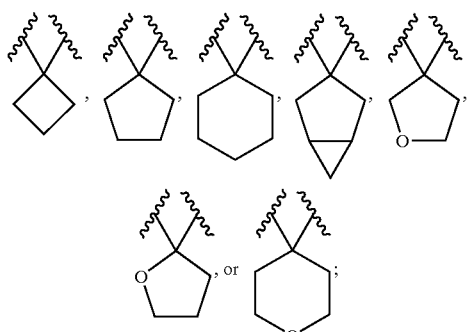

or a pharmaceutically acceptable salt thereof.

25. The compound according to claim 24, which is a compound of Formula (III):

(III)

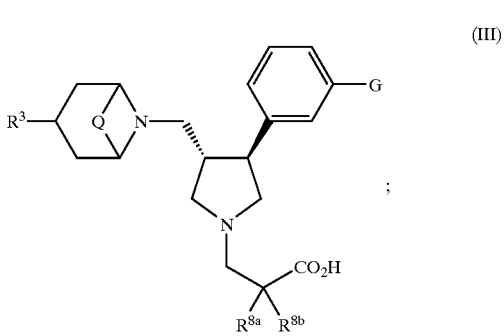

or a pharmaceutically acceptable salt thereof.

26. The compound according to claim 1, which is a compound of Formula (IV):

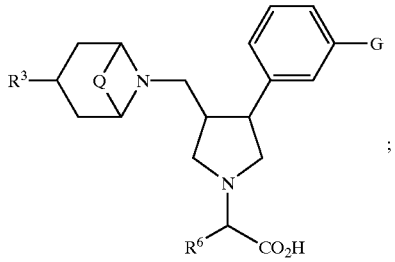

(IV)

wherein
G is hydrogen or fluoro;
Q is —(CH$_2$)$_2$—, —CH$_2$OCH$_2$—, or —CH$_2$SCH$_2$—;
R$^3$ is:

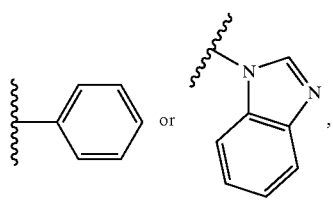

which is optionally substituted with 1–5 substituents where the substituents are independently selected from:
(a) halo,
(b) cyano,
(c) —NO$_2$,
(d) —CF$_3$,
(e) —CHF$_2$,
(f) —CH$_2$F,
(g) phenyl,
(h) C$_{1-6}$ alkyl, which is unsubstituted or substituted with phenyl, which is unsubstituted or substituted with 1–4 of R$^{13}$ where R$^{13}$ is independently selected from halo, cyano, hydroxy, —O—C$_{1-6}$ alkyl, —CO$_2$H, —CO$_2$(C$_{1-6}$ alkyl), and trifluoromethyl, and
(i) —O—C$_{1-6}$ alkyl;
R$^6$ is isopropyl, isobutyl, sec-butyl, t-butyl, cyclohexyl, cyclopentyl, cyclobutyl, cyclopropyl, —CH$_2$-cyclohexyl, —CH$_2$-cyclopentyl, —CH$_2$-cyclobutyl, and —CH$_2$-cyclopropyl;
or a pharmaceutically acceptable salt thereof.

27. The compound according to claim 26, which is a compound of Formula (V):

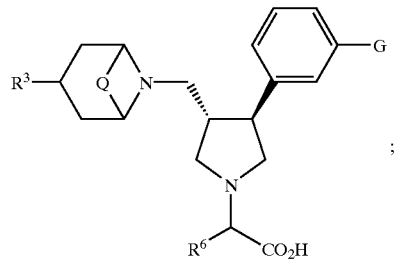

(V)

or a pharmaceutically acceptable salt thereof.

28. The compound according to claim 1, which is a compound selected from the group consisting of:

(2R)-[(3R,4S)-3-{[3-exo-(1H-Benzimidazo-1-yl)-8-azabicyclo[3.2.1]oct-8-yl]methyl}-4-(3-fluorophenyl)pyrrolidin-1-yl](cyclohexyl)ethanoic acid;
(2R)-Cyclohexyl((3S,4R)-3-(3-fluorophenyl)-4-{[3-exo-(2-methyl-1H-benzimidazol-1-yl)-8-azabicyclo[3.2.1]oct-8-yl]methyl}pyrrolidin-1-yl)ethanoic acid;
(2R)-Cyclohexyl[(3R,4S)-3-{[3-exo-(2-ethyl-1H-benzimidazol-1-yl)-8-azabicyclo[3.2.1]oct-8-yl]methyl}-4-(3-fluorophenyl)pyrrolidin-1-yl]ethanoic acid;
(2R)-[(3R,4S)-3-{[3-endo-(1H-Benzimidazol-1-yl)-8-azabicyclo[3.2.1]oct-8-yl]methyl}-4-(3-fluorophenyl)pyrrolidin-1-yl](cyclohexyl)ethanoic acid;
(2R)-Cyclohexyl((3S,4R)-3-(3-fluorophenyl)-4-{[3-endo-(2-methyl-1H-benzimidazol-1-yl)-8-azabicyclo[3.2.1]oct-8-yl]methyl}pyrrolidin-1-yl)ethanoic acid;
(2R)-Cyclohexyl[(3R,4S)-3-{[3-endo-(2-ethyl-1H-benzimidazo-1-yl)-8-azabicyclo[3.2.1]oct-8-yl]methyl}-4-(3-fluorophenyl)pyrrolidin-1-yl]ethanoic acid;
1-{[(3R,4S)-3-{[3-exo-(1H-Benzimidazo-1-yl)-8-azabicyclo[3.2.1]oct-8-yl]methyl}-4-(3-fluorophenyl)pyrrolidin-1-yl]methyl}cyclohexanecarboxylic acid;
1-[((3S,4R)-3-(3-Fluorophenyl)-4-{[3-exo-(2-methyl-1H-benzimidazol-1-yl)-8-azabicyclo[3.2.1]oct-8-yl]methyl}pyrrolidin-1-yl)methyl]cyclohexanecarboxylic acid;
1-{[(3R,4S)-3-{[3-exo-(2-Ethyl-1H-benzimidazo-1-yl)-8-azabicyclo[3.2.1]oct-8-yl]methyl}-4-(3-fluorophenyl)pyrrolidin-1-yl]methyl}cyclohexanecarboxylic acid;
1-{[(3R,4S)-3-{[3-endo-(1H-Benzimidazo-1-yl)-8-azabicyclo[3.2.1]oct-8-yl]methyl}-4-(3-fluorophenyl)pyrrolidin-1-yl]methyl}cyclohexanecarboxylic acid;
1-[((3S,4R)-3-(3-Fluorophenyl)-4-{[3-endo-(2-methyl-1H-benzimidazol-1-yl)-8-azabicyclo[3.2.1]oct-8-yl]methyl}pyrrolidin-1-yl)methyl]cyclohexanecarboxylic acid;
1-{[(3R,4S)-3-{[3-endo-(2-Ethyl-1H-benzimidazo-1-yl)-8-azabicyclo[3.2.1]oct-8-yl]methyl}-4-(3-fluorophenyl)pyrrolidin-1-yl]methyl}cyclohexanecarboxylic acid;
9-{[(3R,4S)-1-[(R)-carboxy(cyclohexyl)methyl]-4-(3-fluorophenyl)pyrrolidin-3-yl]methyl}-7-(2-methyl-1H-benzimidazo-1-yl)-3-oxa-9-azabicyclo[3.3.1]nonane;
9-{[(3R,4S)-1-[(R)-carboxy(cyclohexyl)methyl]-4-(3-fluorophenyl)pyrrolidin-3-yl]methyl}-7-(2-methyl-1H-benzimidazo-1-yl)-3-thia-9-azabicyclo[3.3.1]nonane;
7-(1H-benzinmidazo-1-yl)-9-{[(3R,4S)-1-[(R)-carboxy(cyclohexyl)methyl]-4-(3-fluorophenyl)pyrrolidin-3-yl]methyl}-3-thia-9-azabicyclo[3.3.1]nonane;
9-{[(3R,4S)-1-[(R)-carboxy(cyclohexyl)methyl]-4-(3-fluorophenyl)pyrrolidin-3-yl]methyl}-7-(2-ethyl-1H-benzimidazo-1-yl)-3-thia-9-azabicyclo[3.3.1]nonane;
9-{[(3R,4S)-1-[(1-carboxycyclohexyl)methyl]-4-(3-fluorophenyl)pyrrolidin-3-yl]methyl}-7-(2-methyl-1H-benzimidazo-1-yl)-3-oxa-9-azabicyclo[3.3.1]nonane;
9-{[(3R,4S)-1-[(1-carboxycyclohexyl)methyl]-4-(3-fluorophenyl)pyrrolidin-3-yl]methyl}-7-(2-methyl-3H-benzimidazo-3-yl)-3-thia-9-azabicyclo[3.3.1]nonane;
7-(3H-benzimidazol-3-yl)-9-{[(3R,4S)-1-[(1-carboxycyclohexyl)methyl]-4-(3-fluorophenyl)pyrrolidin-3-yl]methyl}-3-thia-9-azabicyclo[3.3.1]nonane;
9-{[(3R,4S)-1-[(1-carboxycyclohexyl)methyl]-4-(3-fluorophenyl)pyrrolidin-3-yl]methyl}-7-(2-ethyl-3H-benzimidazol-3-yl)-3-thia-9-azabicyclo[3.3.1]nonane;
and pharmaceutically acceptable salts thereof.

29. A pharmaceutical composition which comprises an effective amount of a compound according to claim 1 or a pharmaceutically acceptable salt thereof and a pharmaceutically acceptable carrier.

30. A method for modulating chemokine CCR5 receptor activity in a subject which comprises administering to the subject an effective amount of the compound according to claim 1 or a pharmaceutically acceptable salt thereof.

31. A method for preventing infection by HIV, treating infection by HIV, delaying of the onset of AIDS, or treating AIDS in a patient, which comprises administering to the patient of an effective amount of the compound according to claim 1 or a pharmaceutically acceptable salt thereof.

* * * * *